US 6,433,157 B1

(12) United States Patent
Shanafelt et al.

(10) Patent No.: US 6,433,157 B1
(45) Date of Patent: Aug. 13, 2002

(54) POLYNUCLEOTIDES ENCODING T-CELL SELECTIVE INTERLEUKIN-4 AGONISTS

(75) Inventors: Armen B. Shanafelt, Moraga; Jeffrey Greve, Berkeley; Robert Gundel, Walnut Creek, all of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/408,629

(22) Filed: Sep. 30, 1999

Related U.S. Application Data

(62) Division of application No. 08/874,697, filed on Jun. 13, 1997, now Pat. No. 5,986,059.
(60) Provisional application No. 60/036,746, filed on Jan. 27, 1997, and provisional application No. 60/019,748, filed on Jun. 14, 1996.

(51) Int. Cl.$^7$ .......................... C07H 21/04; C12N 15/00
(52) U.S. Cl. ...................................... 536/23.5; 536/23.1
(58) Field of Search ............................. 435/69.1, 320.1, 435/32.5, 252.3, 69, 52; 530/350, 300, 351; 536/23.5, 23.1

(56) References Cited

U.S. PATENT DOCUMENTS

| 5,013,824 A | 5/1991 | Abrams et al. ............. 530/300 |
| 5,017,691 A | 5/1991 | Lee et al. ....................... 535/2 |
| 5,506,107 A | 4/1996 | Cunningham et al. ....... 435/721 |
| 5,723,118 A | 3/1998 | Sebald ........................ 530/351 |

FOREIGN PATENT DOCUMENTS

| WO | 8702990  | 5/1987  | ........... C07K/15/00 |
| WO | 9221029  | 11/1992 | ........... C07K/13/00 |
| WO | 9310235  | 5/1993  | ........... C12N/15/24 |
| WO | 9321308  | 10/1993 | ........... C12N/13/00 |
| WO | 9400491  | 1/1994  | ........... C07K/13/00 |
| WO | 9527052  | 10/1995 | ........... C12N/15/00 |
| WO | 9527732  | 10/1995 | ........... C07K/14/00 |
| WO | 9604306  | 2/1996  | ........... C07K/14/55 |
| WO | 9604388  | 2/1996  | ........... C12N/15/62 |
| WO | 9609323  | 3/1996  | ........... C07K/14/54 |

OTHER PUBLICATIONS

Aversa, G. et al., "An interleukin–4 (IL–4) mutant protein inhibits both IL–4 or IL–13 induced human immunoglobulin G4 (IgG4) and IgE Synthesis and B cell proliferation: support for a common component shared by IL–4 and IL–13 receptors", J. Exp. Med., 178: 2213–2218 (1993).

Bowie, J. U., et al., "Deciphering the Message in Protein Sequences: Tolerance to Amino Acid Substitutions", Science 247: 1306–1310 (Mar. 1990).

Callard, R., et al., "IL–4 and IL–13 receptors: are they one and the same?", Immunology Today, 17(3): 108–110 (1996).

Carr, C., et al., "Disulfide Assignments in Recombinant Mouse and Human Interleukin 4", Biochemistry, 30: 1515–1523 (1991).

Economides, A. et al., "Designer cytokines: targeting actions to cells of choice", Science, 270: 1351–1353 (1995).

Frömmel, C., et al., "An Estimate on the Effect of Point Mutation and Natural Selection on the Rate of Amino Acid Replacement in Proteins", J. Mol. Evol., 21:233–257 (1985).

George, D. G., et al., "Current Methods in Sequence Comparison and Analysis", Macromolecular Sequencing and Synthesis. Selected Method and Applications, pp. 127–149 (1988).

Hilton, D., et al., "Cloning and characterization of a binding subunit of the interleukin–13 receptor that is also a component of the interleukin–4 receptor", PNAS–USA, 93: 497–501 (1996).

Kaushansky, K., et al., "Hematopoietic growth factors: understanding functional diversity in structural terms", Blood, 82(11): 3229–3240 (1993).

Kondo, M. et al., "Sharing of the interleukin–2 (IL–2) receptor g chain between for receptors for IL–2 and IL–4", Science, 262: 1874–1877 (1993).

Kruse, N., et al., "Two distinct functional sites of human interleukin–4 are identified by variants impaired in either receptor binding or receptor activation", EMBO J., 12(13): 5121–5129 (1993).

Kruse, N., et al., "Conversion of human interleukin–4 into a high affinity antagonist by a single amino acid replacement", EMBO J., 11(9): 3237–3244 (1992).

Kruse, N., et al., "Site–directed mutagenesis reveals the importance of disulfide bridges and aromatic residues for structure and proliferative activity of human Interleukin–4", Febs Letters, 286(1–2): 58–60 (Jul. 1991).

(List continued on next page.)

Primary Examiner—Elizabeth C. Kemmerer
Assistant Examiner—Sandra Wegert
(74) Attorney, Agent, or Firm—John W. Mahoney; Melissa A. Shaw

(57) ABSTRACT

The invention is directed to human IL-4 muteins numbered in accordance with wild-type IL-4 having T cell activating activity, but having reduced endothelial cell activating activity. In particular, the invention is related to human IL-4 muteins wherein the surface-exposed residues of the D helix of the wild-type IL-4 are mutated whereby the resulting mutein causes T cell proliferation, and causes reduced IL-6 secretion from HUVECs, relative to wild-type IL-4. This invention realizes a less toxic IL-4 mutant that allows greater therapeutic use of this interleukin. Further, the invention is directed to IL-4 muteins having single, double and triple mutations represented by the designators R121A, R121D, R121E, R121F, R121H, R121I, R121K, R121N, R121P, R121T, R121W; Y124A, Y124Q, Y124R, Y124S, Y124T; Y124A/S125A, T13D/R121E; and R121T/E122F/ Y124Q, when numbered in accordance with wild type IL-4 (His=1). The invention also includes polynucleotides coding for the muteins of the invention, vectors containing the polynucleotides, transformed host cells, pharmaceutical compositions comprising the muteins, and therapeutic methods of treatment.

25 Claims, 14 Drawing Sheets

OTHER PUBLICATIONS

Lakkis, F., et al., "Phe496 and Leu497 are essential for receptor binding and cytotoxic action of the murine interleukin–4 receptor targeted fusion toxin $DAB_{389}$–mIL–4", Prot. Eng., 5(3): 241–248 (1992).

Lewis, C., et al., "Use of a novel mutagenesis strategy, optimized residue substitution, to decrease the off–rate of an anti–gp120 antibody", Mol. Immunol., 32(14): 1065–1072 (1995).

Liblau, R., et al., "Th1 and Th2 CD4+ T cells in the pathogenesis of organ–specific autoimmune diseases", Immunology Today, 16(1): 34–38 (1995).

Lopez, A., et al., "A human interleukin–3 analog with increased biological and binding activities", PNAS(USA), 89:11842–11846 (1992).

Maher, D.W., et al., "Human interleukin–4: an immunomodulator with potential therapeutic applications", Progress in Growth Factor Research , 3: 43056 (1991).

Margolin, K., et al., "Phase II studies of recombinant human interleukin–4 in advanced renal cancer and malignant melanoma", J. Immunotherapy, 15: 147–153 (1994).

Matthews,D., et al., "Function of the interleukin–2(IL–2) receptor g–chain in biologic responses of X–linked severe combined immunodeficient B cellsto IL–2, IL–4, IL–13, and IL–15", Blood 85(1): 38–42 (1995).

Morrison, B., et al., "A receptor binding domain of mouse interleukin–4 defined by a solid–phase binding assay and in vitro mutagenesis", J. Biol. Chem. 267(17): 11957–11963 (1992).

Müller, T., et al., "Human Interleukin–4 and Variant R88Q: Phasing X–ray Diffraction Data by Molecular Replacement Using X–ray and Nuclear Magnetic Resonance Models", J. Mol. Biol., 247: 360–372 (1995).

Ngo, J. T., et al., "Computational Complexity Protein Structure and the Levinthal Paradox", in *The Protein Folding Problem and Teritary Structure Prediction*, K. Mertz and S. Le Grand, eds. (Birkhauser Boston 1994) pp. 433 and 492–495.

Obiri, N., et al., "Receptor for Interleukin 13", J. Biol. Chem., 270(15): 8797–8804 (1995).

Olins, P., et al., "Saturation mutagenesis of human interleukin–3", J. Biol. Chem., 270(40):23754–23760 (1995).

Powers, R., et al., "Three–Dimensional Solution Structure of Human Interleukin–4 by Multidimensional Heteronuclear Magnetic Resonane Spectroscopy", Science 256:1673–1677 (Jun. 1992).

Powrie, F., et al., "Cytokine regulation of T–cell function: potential for therapeutic intervention", Immunology Today 14(6): 270–274 (1993).

Racke, M.K., et al., "Cytokine–induced immune deviation as a therapy for inflammatory autoimmune disease", J. Exp. Med. (USA), 180(5): 1961–1966—Abstract (1994).

Russell, S., et al., "Interleukin–2 receptor g chain: a functional component of the interleukin–4 receptor", Science, 262: 1880–1883 (1993).

Savino, R., et al., "Rational design of a receptor super–antagonist of human interleukin–6", The EMBO Journal, 13(24): 5863–5870 (1994).

Savino, R., et al., "Saturation mutagenesis of the human interleukin–6 receptor–binding site: implications for its three–dimensional structure", PNAS (USA), 90: 4067–4071 (1993).

Schnyder, B., et al., "Interleukin–4 (IL–4) and IL–13 bind to a shared heterodimeric complex on endothelial cells mediating vascular cell adhesion molecule–1 induction in the absence of the common g chain", Blood, 87(10): 4286–4295 (1996).

Tony, H–P., et al., "Design of human interleukin–4 antagonists inhibiting interleukin–4–dependent and interleukin–13–dependent responses in T–cells and B–cells with high efficiency", E. J. Biochem., pp. 659–665 (1994).

Walter, et al., "Crystal structure of a complex between interferon–g and its soluble high–affinity receptor", Nature, 376: 230–235 (1995).

Wlodawer, A., et al., "Hematopoietic cytokines: similarities and differences in the structures, with implications for receptor binding", Protein Science, 2: 1373–1382 (1993).

Zurawski, S., et al., "Receptors for interleukin–13 and interleukin–4 are complex and share a novel component that functions in signal transduction", The EMBO Journal, 12(7): 2663–2670 (1993).

Bork, P. (1996), Go hunting in sequence databases but watch out for the traps. Trends Genetics, 12(10):425–427.*

Bork, P. (1998), Powers and Pitfalls in Sequence Analysis: The 70% Hurdle. Genome Res., 10:398–400, esp. p. 400.*

Doerks, T. (1998), Protein annotation: detective work for function prediction. Trends Genetics. 14(6):248–250.*

Skolnick, J. (2000), From genes to protein structure and function: novel applications of computational approaches in the genomic era., trends Biotech., 18(1):34–39, esp. p. 36.*

Brenner, S. (1999) Errors in genome annotation, Trends in Genetics, 15(4): 3–4, esp. Fig. 2.*

Smith, T.F., and Xhang, X. (1997) The challenges of genome sequence annotation or "The devil is in the details", Nature Biotechnology, 15: 1222–1223.*

* cited by examiner

SEQ ID NO:1:

```
                    Helix A →
His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr
                20                  25                  30

Helix B →
Asp Ile Phe Ala Ala Ser Lys Asn Thr Thr Glu Lys Glu Thr Phe
                35                  40                  45

Cys Arg Ala Ala Thr Val Leu Arg Gln Phe Tyr Ser His His Glu
                50                  55                  60

Helix C →
Lys Asp Thr Arg Cys Leu Gly Ala Thr Ala Gln Gln Phe His Arg
                65                  70                  75

His Lys Gln Leu Ile Arg Phe Leu Lys Arg Leu Asp Arg Asn Leu
                80                  85                  90

Trp Gly Leu Ala Gly Leu Asn Ser Cys Pro Val Lys Glu Ala Asn
                95                  100                 105

Helix D →
Gln Ser Thr Leu Glu Asn Phe Leu Glu Arg Leu Lys Thr Ile Met
                110                 115                 120

Arg Glu Lys Tyr Ser Lys Cys Ser Ser
                125
```

FIG._1

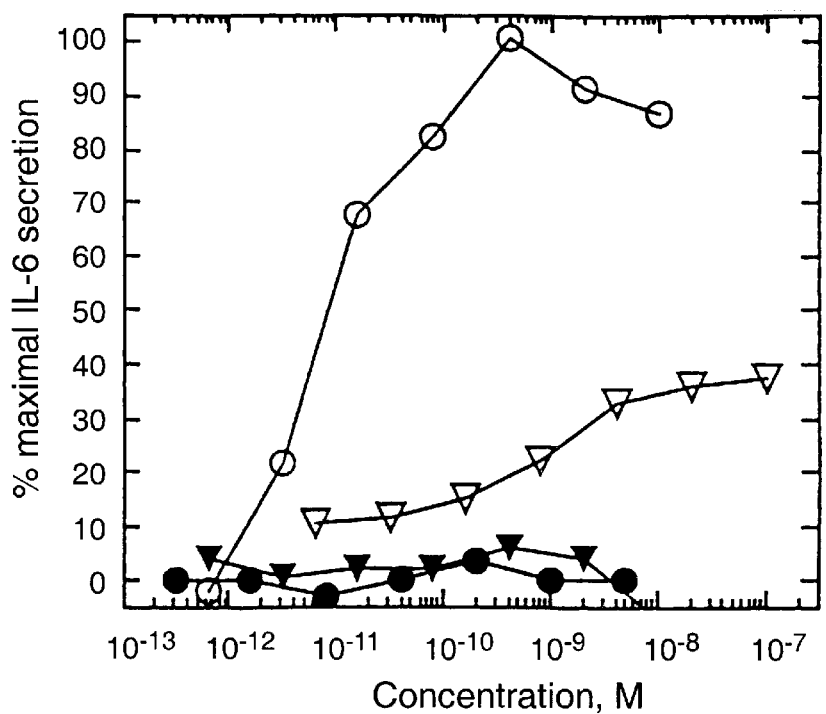
FIG._3A
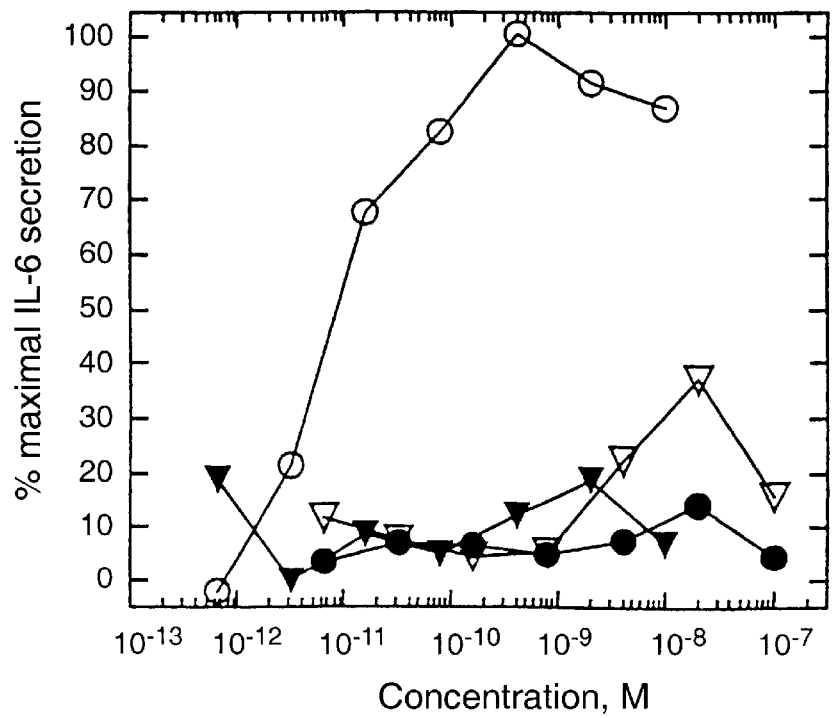
FIG._3B

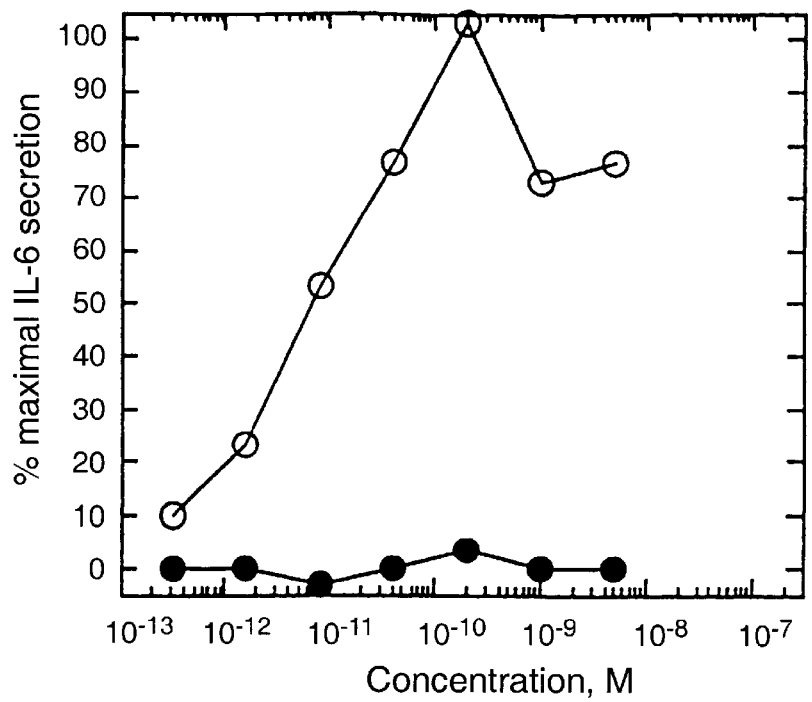
FIG._4A
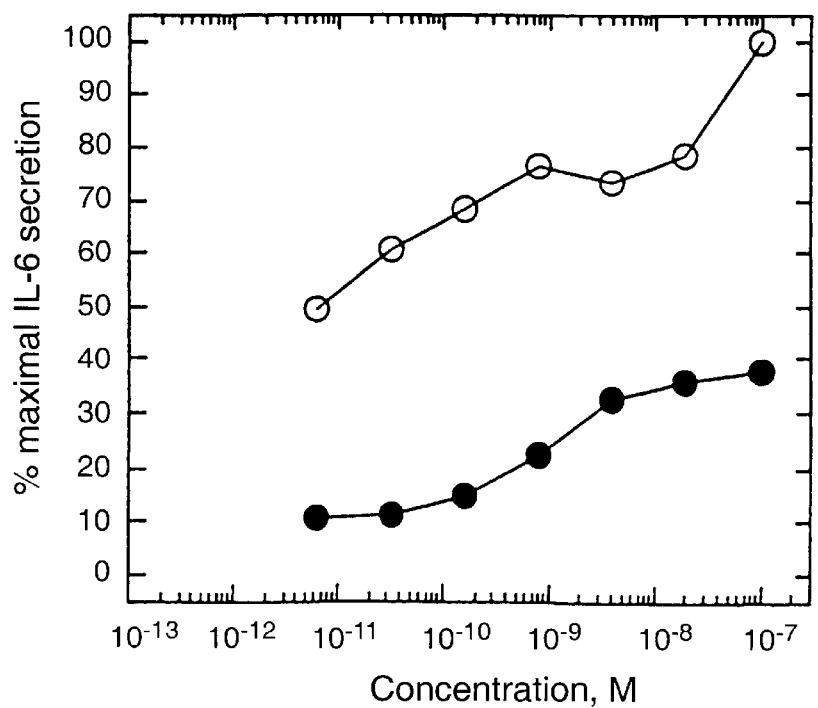
FIG._4B

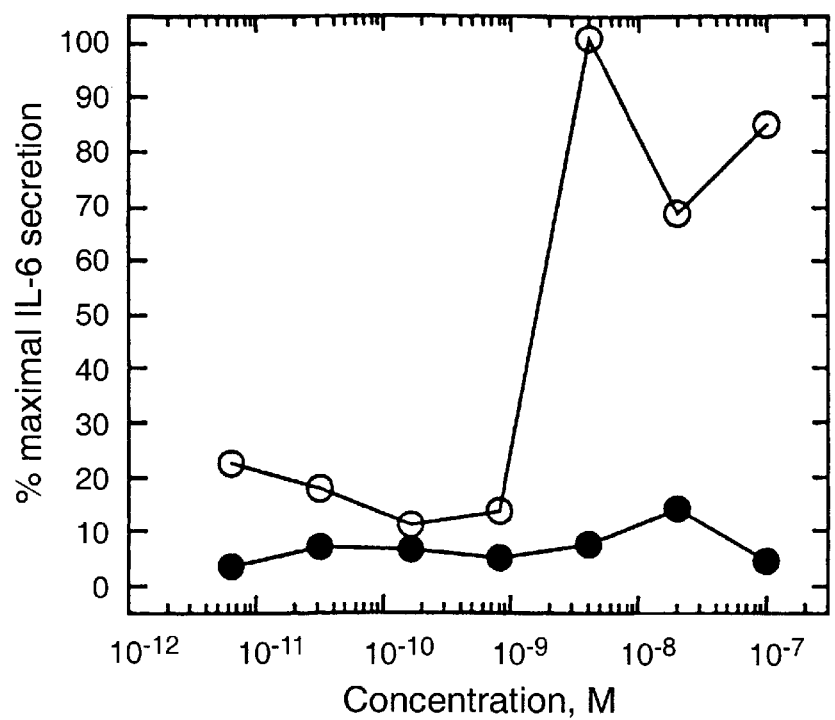
FIG._4C
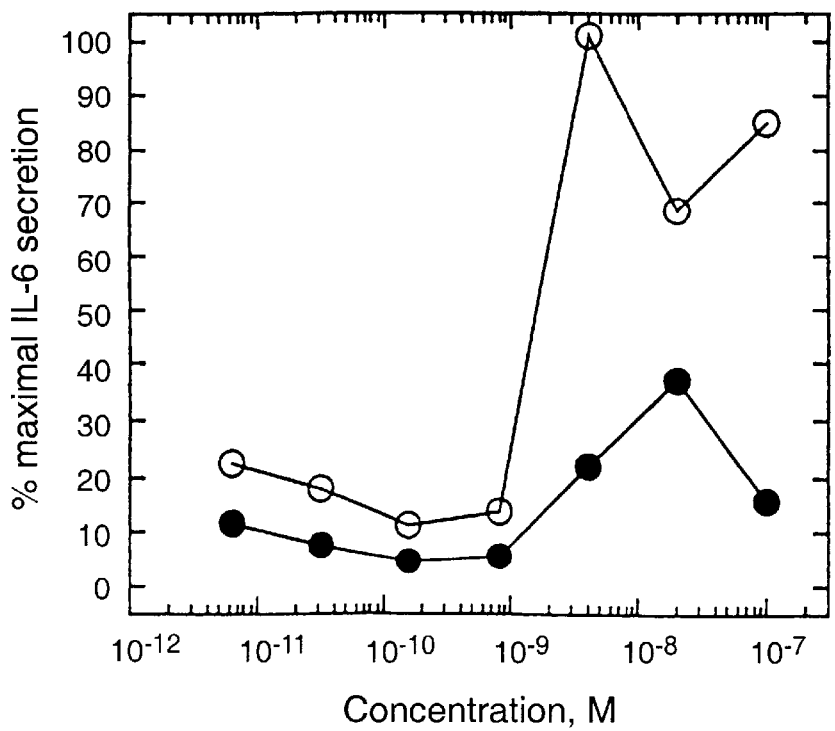
FIG._4D

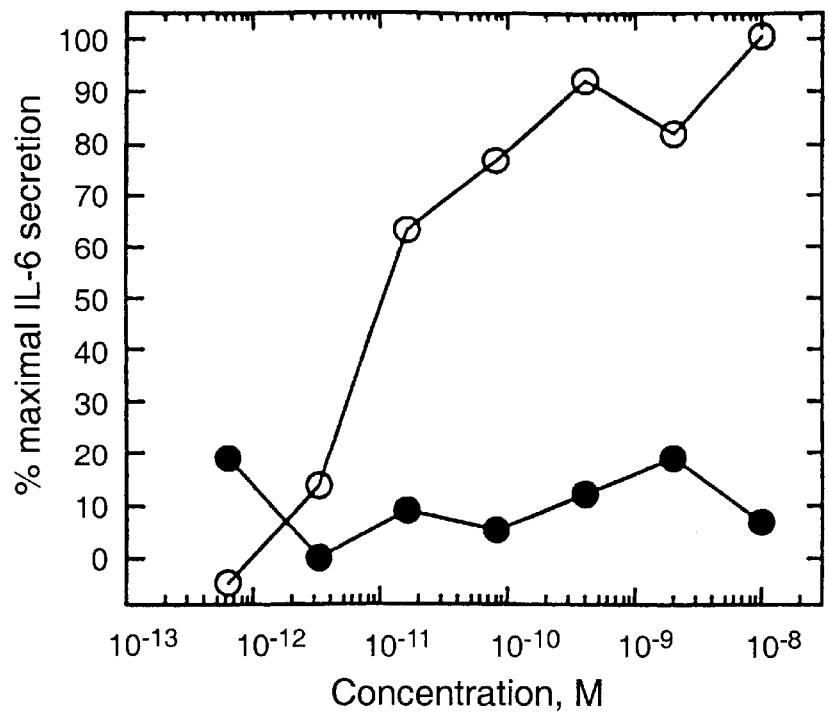
FIG._4E
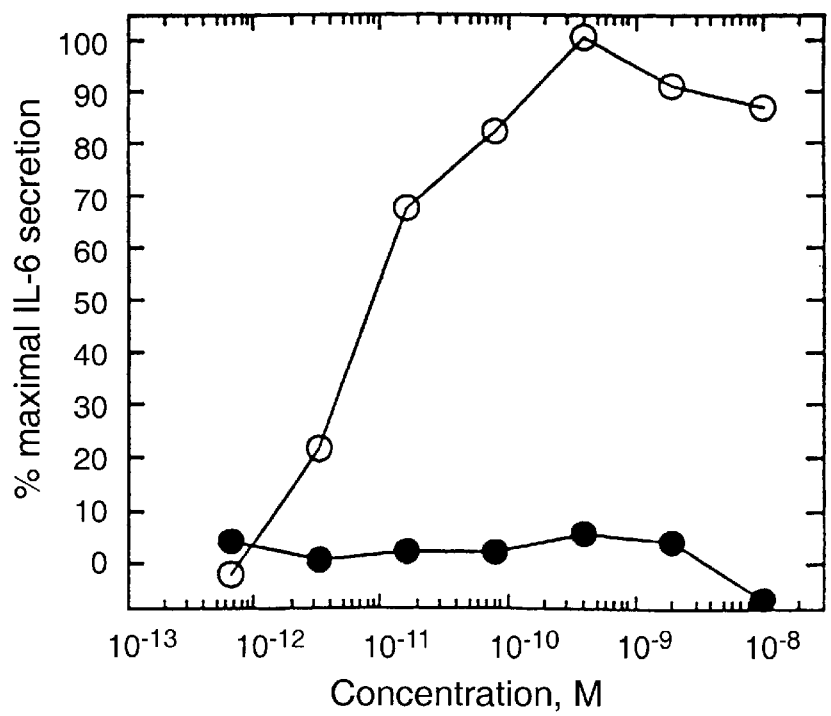
FIG._4F

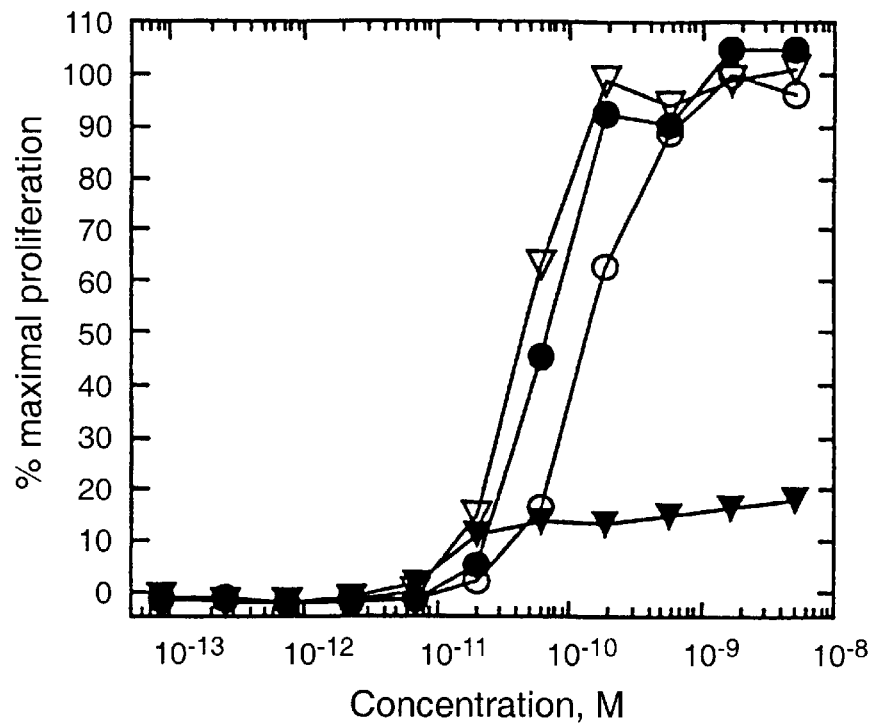
FIG._5A
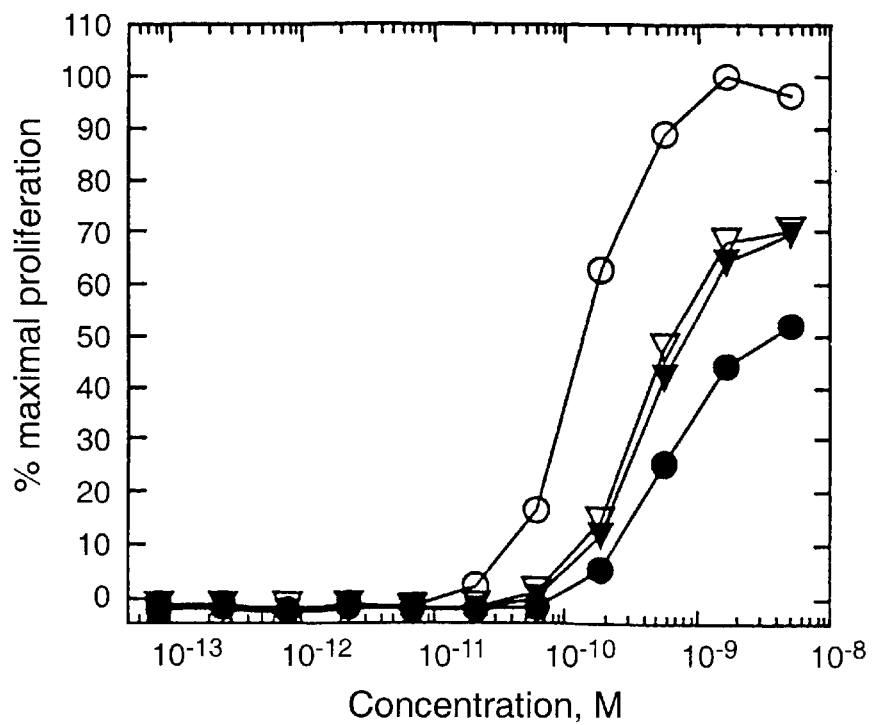
FIG._5B

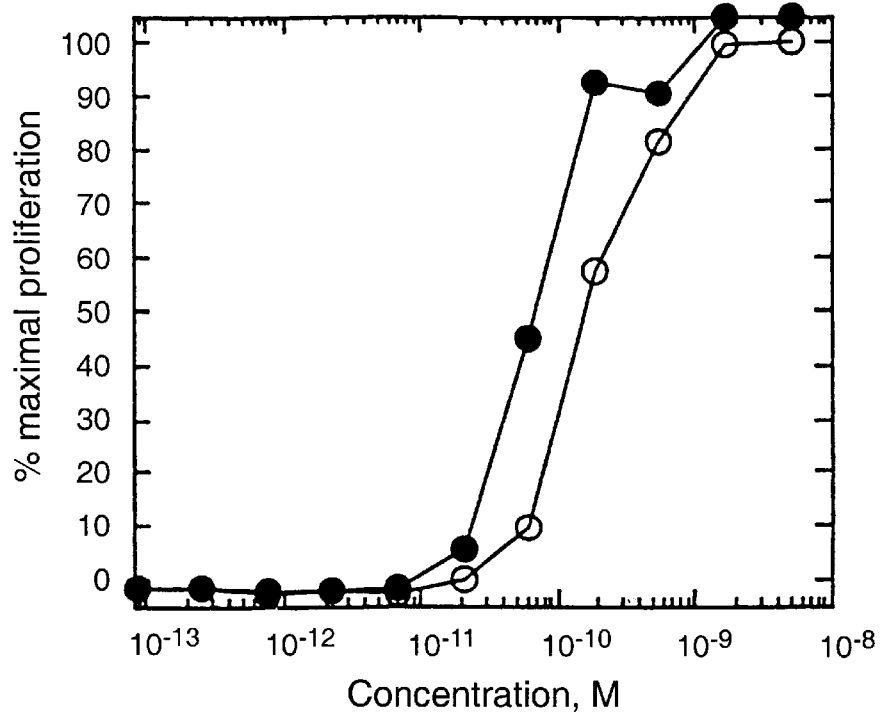
FIG._6A
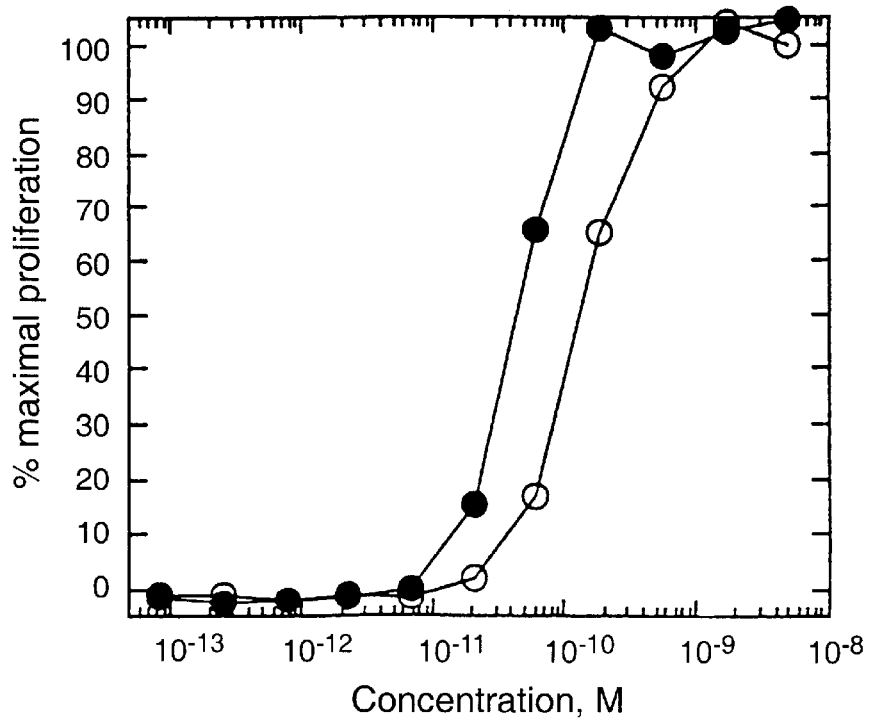
FIG._6B

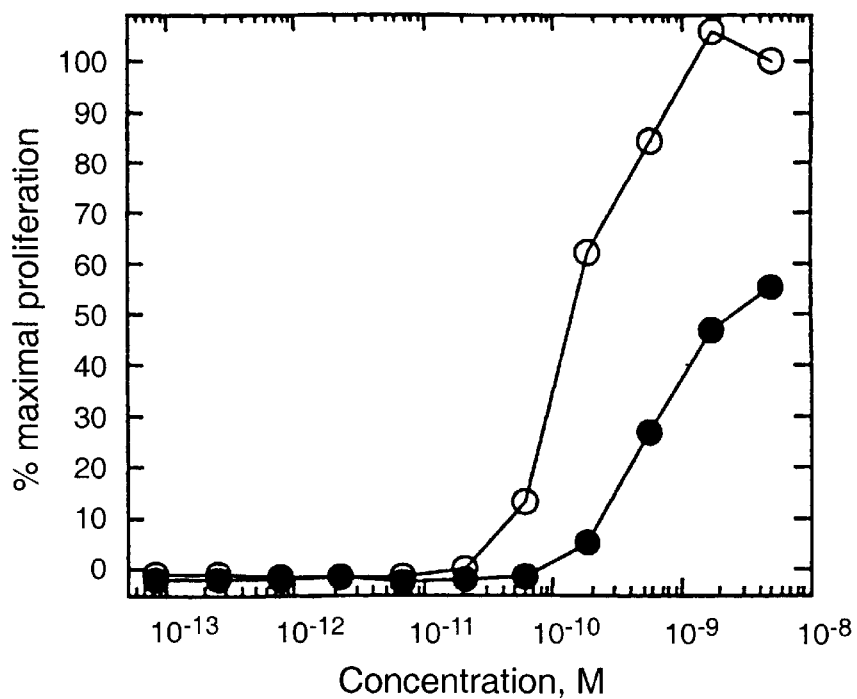
FIG._6C
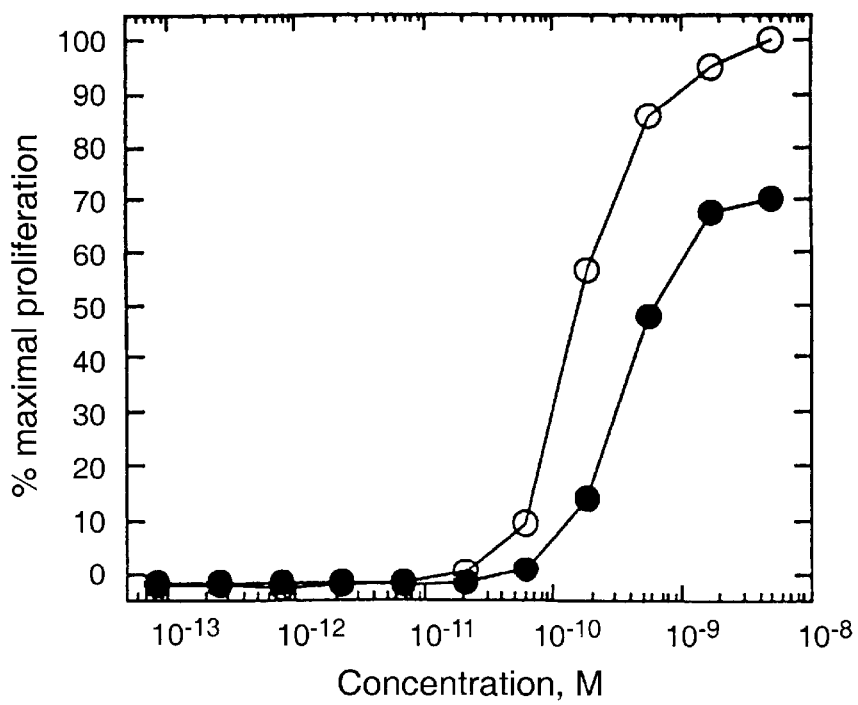
FIG._6D

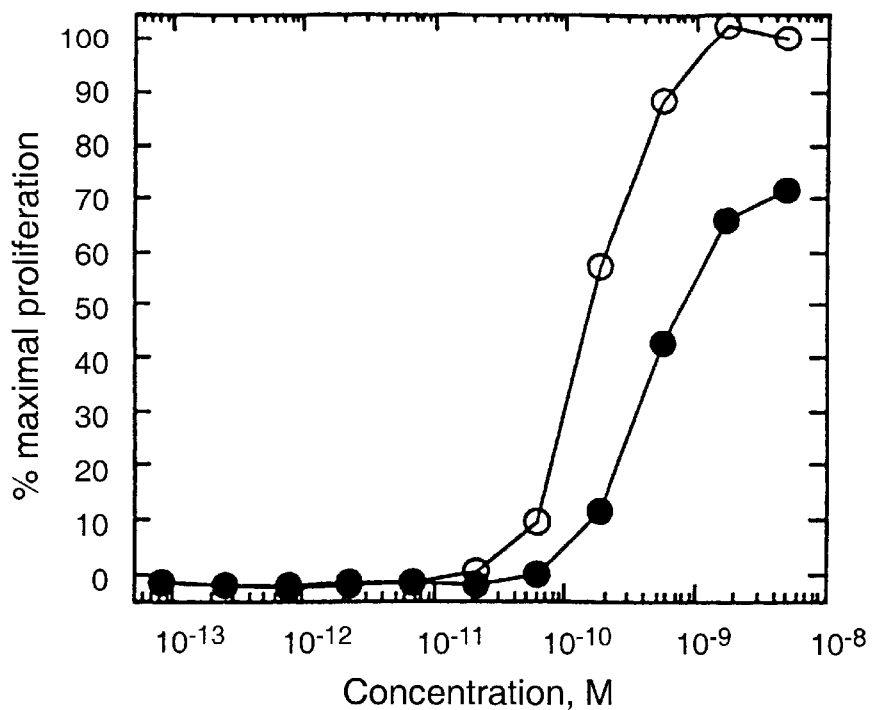
FIG._6E
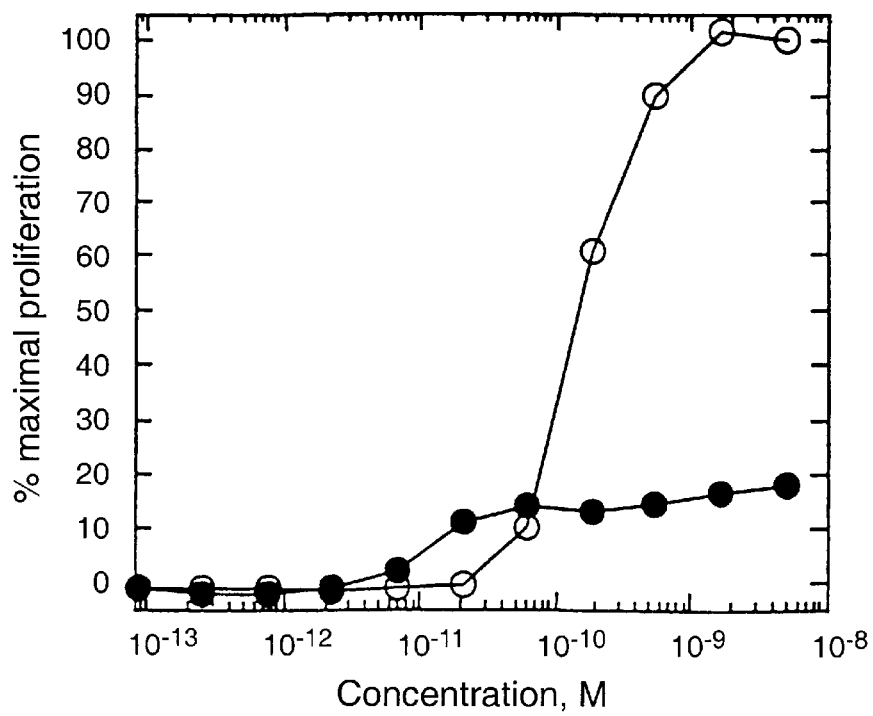
FIG._6F

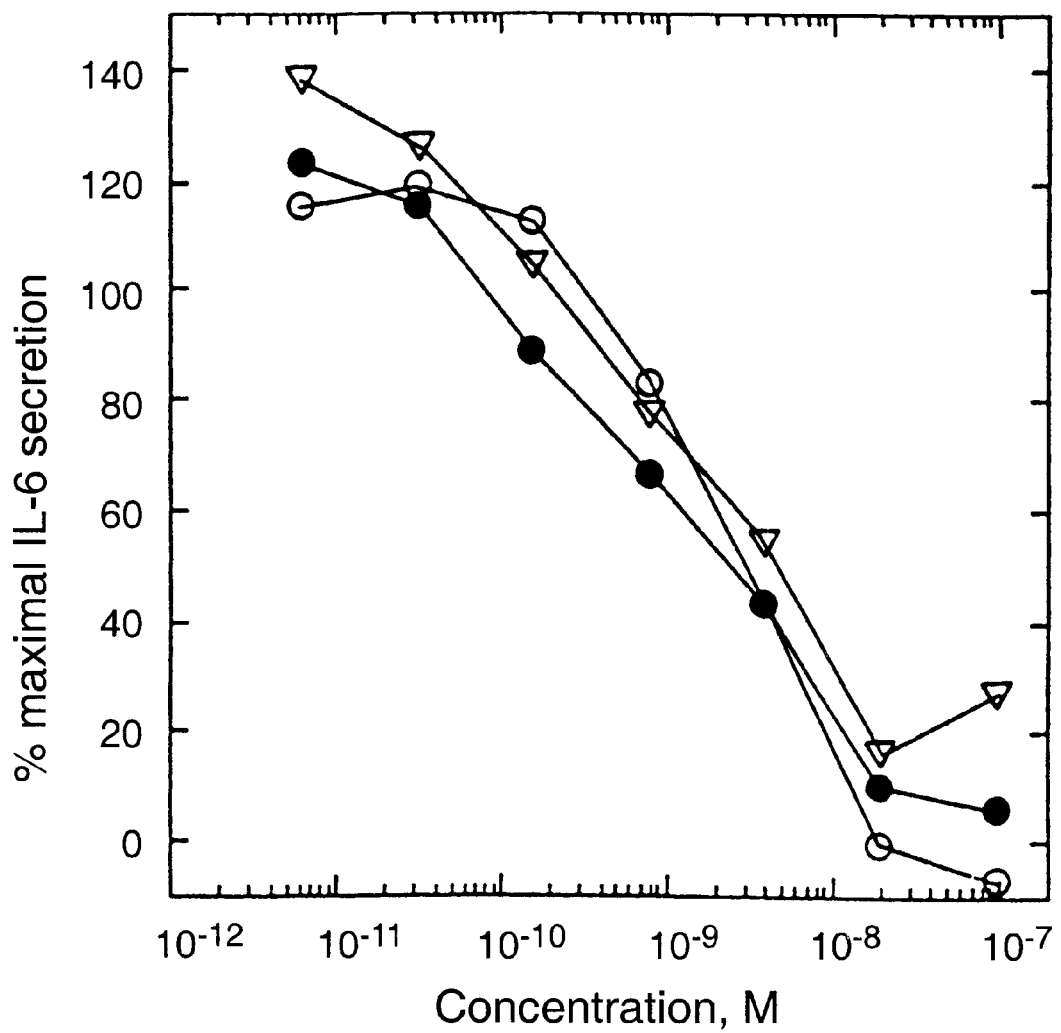
FIG._7

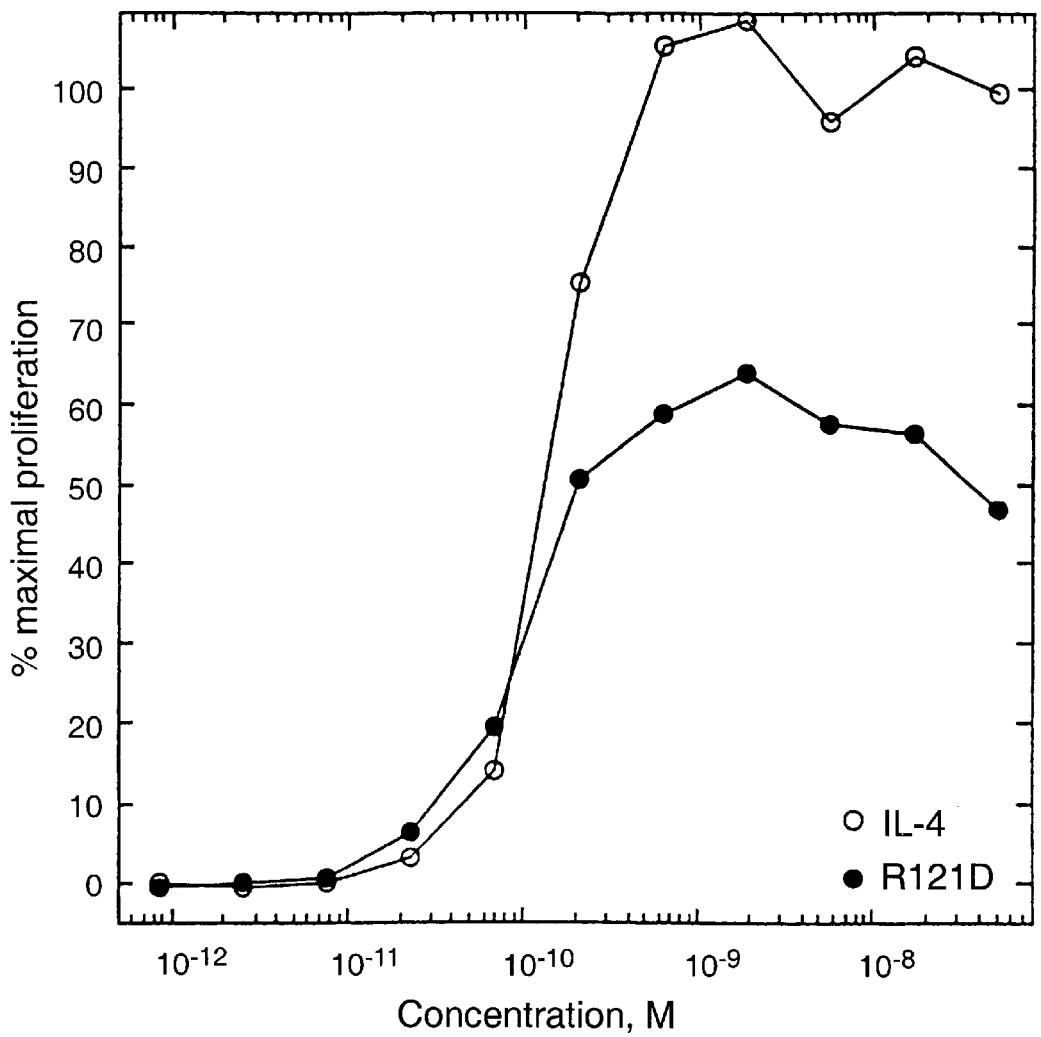
FIG._8A

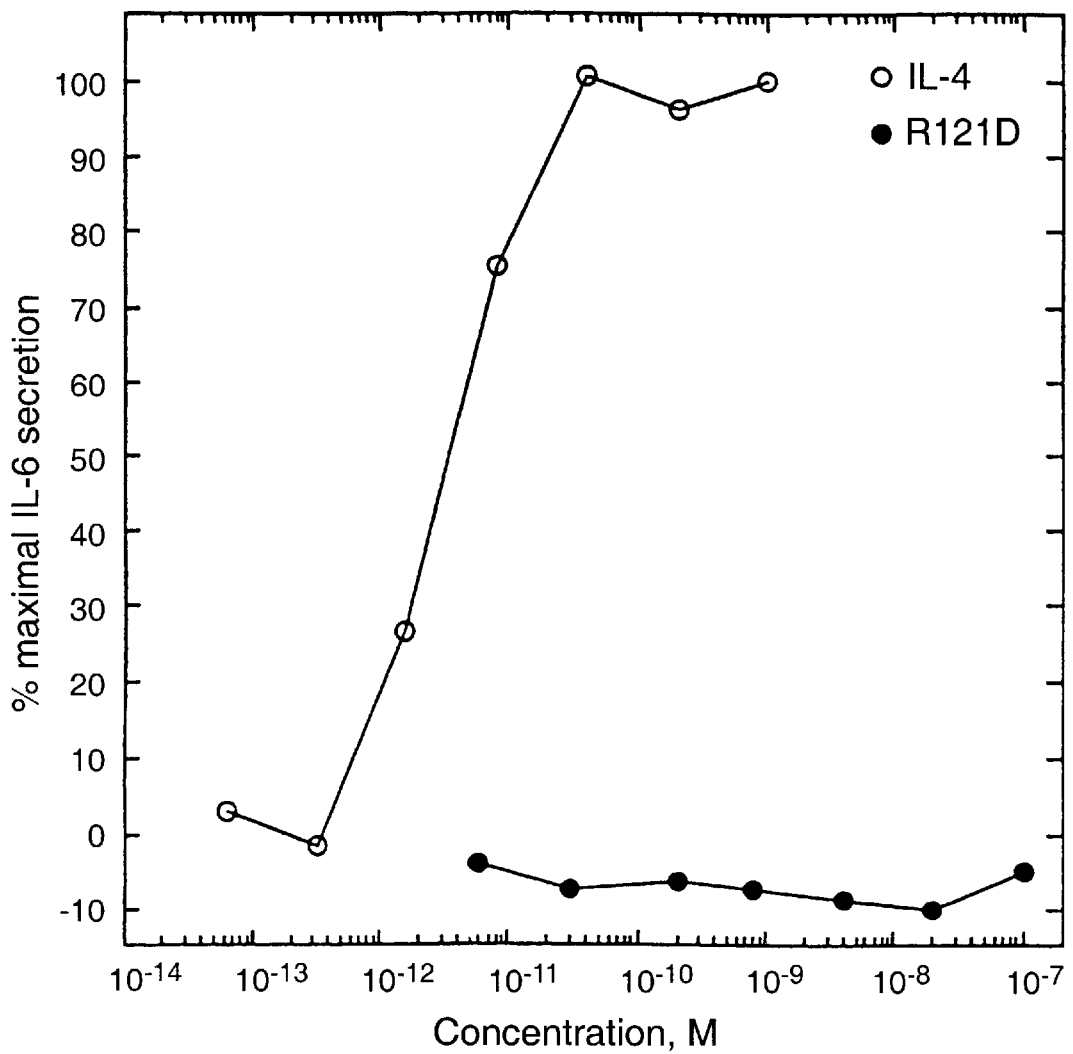
FIG._8B

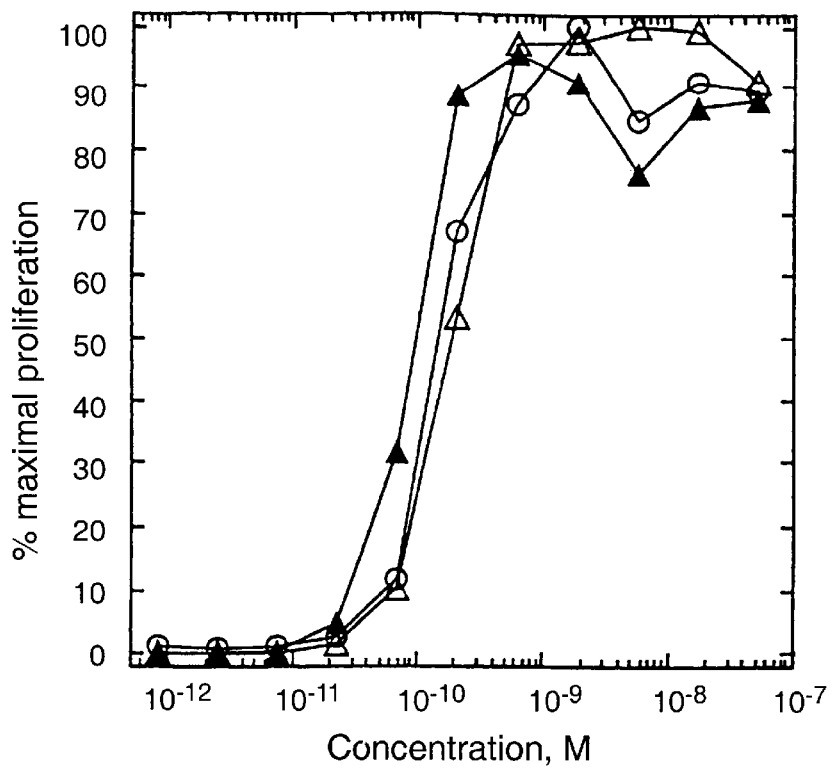
FIG._9A
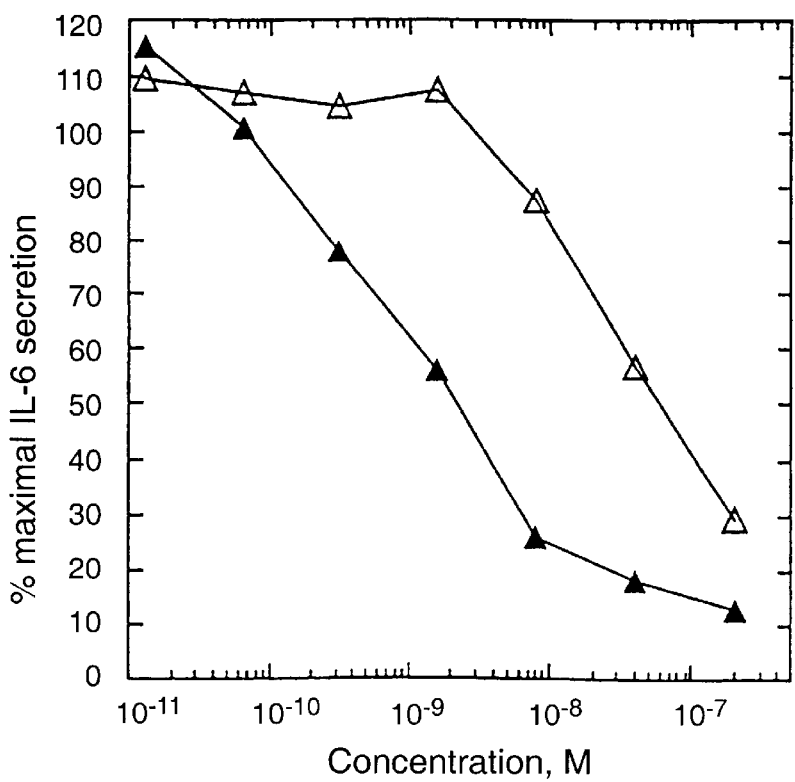
FIG._9B

POLYNUCLEOTIDES ENCODING T-CELL SELECTIVE INTERLEUKIN-4 AGONISTS

CROSS REFERENCE TO RELATED APPLICATIONS

This application is a division of U.S. Ser. No. 08/874,697 filed Jun. 13, 1997, now U.S. Pat. No. 5,986,059 and claims the benefit of Provisional Application No. 60/019,748 filed Jun. 14, 1996 and No. 60/036,746 filed Jan. 27, 1997, abandoned.

BACKGROUND

1. Field of the Invention

The invention is generally related to the fields of pharmacology and immunology. More specifically, the invention is directed to novel compositions of matter for selectively activating T cells, and having reduced activation of Endothelial cells or fibroblasts. The novel compositions include variants of the cytokine family, and in particular human Interleukin-4 (IL-4).

2. Description of Related Art

Interleukin 4 (IL-4) is a pleiotropic cytokine, having activities on cells of the immune system, endothelium, and those of fibroblastic nature. Reported in vitro effects of IL-4 administration include proliferation of B cells, immnunoglobulin class switching in B cells. In T cells, IL-4 stimulates T cell proliferation after preactivation with mitogens and down-regulates IFN-γ production. In monocytes, IL-4 induces class II MHC molecules expression, release of lipopolysaccharide-induced tPA, and CD23 expression. In Endothelial cells (EC), IL-4 induces expression of VCAM-1 and IL-6 release, and decreases ICAM-1 expression. (Maher, D W, et al., Human Interleukin-4: An Immunomodulator with Potential Therapeutic Applications, *Progress in Growth Factor Research*, 3:43–56 (1991)).

Because of its ability to stimulate proliferation of T cells activated by exposure to IL-2, IL-4 therapy has been pursued. For instance, IL-4 has demonstrated anti-neoplastic activity in animal models of renal carcinomas, and has induced tumor regression in mice (Bosco, M., et al., Low Doses of IL-4 Injected Perilymphatically in Tumor-bearing Mice Inhibit the Growth of Poorly and Apparently Nonimmunogenic Tumors and Induce a Tumor Specific Immune Memory, *J. Immunol.*, 145:3136–43 (1990)). However, its toxicity limits dosage in humans (Margolin, K, et al., Phase II Studies of Human Recombinant Interleukin-4 in Advanced Renal Cancer and Malignant Melanoma, *J. Immunotherapy*, 15:147–153 (1994)).

Because of its immunoregulatory activity, a number of clinical applications are suggested for IL-4. Among these clinical applications are disorders caused by imbalances of the immune system, particulary those caused by imbalances of T helper (Th) cell responses to antigen. These diseases include certain autoimmune diseases, rheumatic diseases, dermatological diseases, and infectious diseases. A large body of experimental work has established that Th cells fall into two broad classes, designated Th1 and Th2 (Mosmann, T. R., Cherwinski, H., Bond, M. W., Giedlin, M A. and Coffinan, R. L., Two types of murine helper T cell clone. I. Definition according to profiles of lymphokine activities and secreted proteins, *J. Immunol.*, 136:2348–2357 (1986); Mosmann, T. R., Cytokines, differentiation and functions of subsets of CD4 and CD8 T cells, *Behring Inst. Mitt.*, 1–6 (1995)). These T cell classes are defined by the cytokines they express: Th1 cells make IL-2, INF-γ, and TNF-α, while Th2 cells make IL-4 and IL-5. Th1 and Th2 cells are formed from naive CD4+T cells. Differentiation into Th1 or Th2 subsets depends on the cytokine present during antigen stimulation: IFN-γ and IL-12 direct differentiation of naive cells to the Th1 phenotype, while IL-4 directs differentiation to the Th2 phenotype. While the Th1 and Th2 subsets may represent extremes along a continuum of Th cell phenotypes (for example, Th0 cells, which express low levels of both INF-γ and IL-4, have been described), this classification nevertheless is the major paradigm in the field of immunology for describing the character of the immune response.

It has been observed that certain organ-specific autoimmune diseases are associated with a predominantly Th1 T cell response against autoantigen (Liblau R S; Singer S M;, McDevitt H O, Th1 and Th2 CD4$^+$ T cells in the pathogenesis of organ-specific autoimmune diseases, *Immunol. Today*, 16:34–38 (1995)). One such autoimmune disease is insulin-dependent diabetes (IDDM), a disorder characterized by T cell-mediated destruction of pancreatic β cells. Several lines of evidence suggest that Th1-type cells are primarily responsible for the pancreatic β cell destruction (reviewed in Tisch, R. et al., Review: Insulin-dependent Diabetes Mellitus, *Cell*, 85:291–297 (1996)). Administration of IL-4 to NOD mice, which serves as an animal model of IDDM, down-regulates the Th1 cell population and significantly delays the onset of diabetes (Rapoport, et al., IL-4 Reverses T cell Proliferation Unresponsiveness and Prevents the Onset of Diabetes in NOD Mice, *J. Exp. Med.,* 178:87–99 (1993)). Another such autoimmune disease is multiple sclerosis (MS), a disease which is characterized by an autoimmune attack upon the myelin sheath surrounding nerve cells. Studies in humans with MS have demonstrated that exacerbation of MS is associated with the presence of autoantigen-specific Th1 and Th0 cells and that remission is associated with the presence of autoantigen-specific Th2 and Th0 cells (Correale, J et al., Patterns of cytokine secretion by autoreactive proteolipid protein-specific T cell clones during the course of multiple sclerosis, *J. Immunol.,* 154:2959–2968 (1995)). Mice with experimental autoimmune encephalomyelitis (EAE), an animal model for MS, also exhibit the Th1 cell polarization (Cua, D J, Hinton, D R, and Stohlman, S A, *J. Immunol.,* 155:4052–4059 (1995)). Indirect evidence from a study in the EAE model suggests that IL-4 plays a critical role in disease attenuation resulting from treatment with a tolerogenic peptide (Brocke, S. et al. Treatment of experimental encephalomyelitis with a peptide analogue of myelin basic protein, *Nature,* 379:343–346 (1996)).

Other autoimmune diseases such as Rheumatoid Arthritis (RA) are also targets for IL-4 based therapies. Animal models of RA have shown a disequilibrium of cell profiles tilting towards Th1 cells, and in mice that overexpress TNF-α, anti-TNF-α antibodies have demonstrated disease attenuation, suggesting that IL-4 therapies that result in down-regulation of Th1 cell populations may have an anti-TNF-α effect also. (See Feldmann, M, et al., Review: Rheumatoid Arthritis, *Cell,* 85:307–310 (1996)).

Psoriasis vulgaris is a chronic dermatologic disorder characterized by infiltration of affected skin with monocytes and T cells. Several reports indicate that psoriatic skin lesional T cells and PBL are predominantly of the Th1 phenotype (Uyemura K; Yamamura M; Fivenson D F; Modlin R L; Nickoloff B J, The cytokine network in lesional and lesion-free psoriatic skin is characterized by a T-helper type 1 cell-mediated response, *J Invest Dermatol.,* 101:701–705 (1993); Schlaak J F; Buslau M; Jochum W, Hermann E; Girndt M; Gallati H; Meyer zum Buschenfelde K H; Fleischer B, T cells involved in psoriasis vulgaris belong to the Th1 subset, *J Invest Dermatol,* 102:145–149 (1994)). Furthermore, monomethylfumarate, a drug which has been reported to be of clinical benefit to patients with psoriasis, has been shown to selectively stimulate Th2 cytokine secretion from PBMC (de Jong R; Bezemer A C; Zomerdijk T P; van de Pouw-Kraan T, Ottenhoff T H; Nibbering P H, Selective stimulation of T helper 2 cytokine responses by the anti-psoriasis agent monomethylfumarate, *Eur J Immunol,* 26:2067–2074 (1996)). Therefore, IL-4 would be expected to reverse the Th polarization and be of clinical benefit in psoriasis.

Certain infectious diseases are associated with polarized Th cell responses to the infectious agent. Th2 responses have in some cases been associated with resistance to the infectious agent. An example is *Borrelia burgdorfei,* the infectious agent for Lyme disease. Humans infected with *B. burgdorferi* exhibit a predominantly Th1 -like cytokine profile (Oksi J; Savolainen J; Pene J; Bousquet J; Laippala P; Viijanen M K, Decreased interleukin-4 and increased gamma interferon production by peripheral blood mononuclear cells of patients with Lyme borreliosis, *Infect. Immun.,* 64:3620–3623 (1996)). In a mouse model of *B. burgdoreri*-induced arthritis, resistance to disease is associated with IL-4 production while susceptibility is associated with INF-γ production (Matyniak J E; Reiner S L, T helper phenotype and genetic susceptibility in experimental Lyme disease, *J Exp Med,* 181(3):1251–1254 (1995); Keane-Afyers A; Nickell S P, Role of IL-4 and IFN-gamma in modulation of immunity to *Borrelia burgdorferi* in mice, *J Immunol,* 155:2020–2028 (1995)). Treatment of *B. burgdorferi*-infected mice with IL-4 augments resistance to the infection (Keane-Myers A; Maliszewski C R; Finkelman F D; Nickell S P, Recombinant IL-4 treatment augments resistance to *Borrelia burgdorferi* infections in both normal susceptible and antibody-deficient susceptible mice, *J Immunol.,* 156:2488–2494(1996)).

IL-4 has been reported to have a direct effect on inhibiting the growth of lymphomas and leukemias (Akashi, K, The role of interleukin-4 in the negative regulation of leukemia cell growth, *Leuk Lymphoma,* 9:205–9 (1993)). For example, IL-4 has been reported to induce apoptosis in cells from patients with acute lymphoblastic leukemia (Manabe, A, et al., Interleukin-4 induces programmed cell death (apoptosis) in cases of high-risk acute lymphoblastic leukemia, *Blood,* 83:1731–7 (1994)), and inhibits the growth of cells from patients with non-Hodgkin's B cell lymphoma (Defrance, T, et al., Antiproliferative effects of interleukin-4 on freshly isolated non-Hodgkin malignant B-lymphoma cells, *Blood,* 79:990–6 (1992)).

IL-4 has also been reported to exhibit activities which suggests that it would be of clinical benefit in osteoarthritis. Osteoarthritis is a disease in which the degradation of cartilage is the primary pathology (Sack, K E, *Osteoarthritis,* A continuing challenge, *West J Med,* 163:579–86 (1995); Oddis, C V, New perspectives on osteoarthritis, *Am J Med,* 100:10S–15S (1996)). IL-4 inhibits TNF-α and IL-1 beta production by monocytes and synoviocytes from osteoarthritic patients (Bendrups, A, Hilton, A, Meager, A and Hamilton, J A, Reduction of tumor necrosis factor alpha and interleukin-1 beta levels in human synovial tissue by interleukin-4 and glucocorticoid, *Rheumatol Int,* 12:217–20 (1993); Seitz, M, et al., Production of interleukin-1 receptor antagonist, inflammatory chemotactic proteins, and prostaglandin E by rheumatoid and osteoarthritic synoviocytes—regulation by IFN-gamma and IL-4, *J Immunol,* 152:2060–5 (1994)). Additionally, IL-4 has been reported to directly block the degradation of cartilage in ex vivo cartilage explants (Yeh, L A, Augustine, A J, Lee, P, Riviere, L R and Sheldon, A, Interleukin-4, an inhibitor of cartilage breakdown in bovine articular cartilage explants, *J Rheumatol,* 22:1740–6 (1995)). These activities suggest that IL-4 would be of clinical benefit in osteoarthritis.

However, the clinical use of IL-4 has been limited due to its acute toxicity, which is manifested as a vascular leak syndrome (Margolin, K, et al., Phase II Studies of Human Recombinant Interleukin-4 in Advanced Renal Cancer and Malignant Melanoma, *J. Immunotherapy,* 15:147–153 (1994)). There is no art in the literature which describes the mechanism of the acute toxic effect of IL-4, nor that describes analogs or mutants of IL-4 that retain immunoregulatory activities but have reduced acute toxicity.

IL-4 mutant proteins ("muteins") are known. The IL-4 mutein IL-4/Y 124D is a T cell antagonist (Kruse N, Tony H P, Sebald W, Conversion of human interleukin-4 into a high affinity antagonist by a single amino acid replacement, *Embo J,* 11:3237–44 (1992)).

Therapeutic uses of IL-4 found in patents or patent applications include the following: the use of IL-4 for potentiation of anticancer effects of chemotherapeutic agents, particularly Hodgkin's Disease and non-Hodgkins Lymphoma (see WO 9607422); the use of antigenic fragments of IL-4 to generate antibodies to treat IL-4 related diseases by suppressing or imitating the binding activity of IL-4 (see WO 9524481), and to detect, measure and immunopurify IL-4 (see WO 9317106); for inducing the differentiation of precursor B cells to Immunoglobulin secreting cells, the mature B cells being useful for restoring immune function in immune-compromised patients (see WO 9404658); when used in combination with IL-10, as a therapy for treatment of leukemia, lymphoma, inflammatory bowel disease and delayed type hypersensitivity (e.g. ulcerative colitis and Crohn's Disease) (see WO 9404180); treatment of HIV infection by administering IL-4 to inhibit viral replication in monocytes and macrophages, and to increase their cytotoxicity towards some tumor cells (see WO 9404179); for stimulation of skin fibroblast proliferation for treating wounds in diabetic and immunocompromised patients (see WO 9211861); for enhancing the primary immune response when administering bacterial, toxoid, and viral vaccines, especially tetanus toxoid vaccine (see WO 9211030); for inhibition of IL-2 induced proliferation of B cell malignancies, especially chronic lymphocytic leukemia, non-Hodgkin's malignant lymphoma (see WO 9210201); use of IL-4 to treat melanomas, renal and basal cell carcinomas (see WO 9204044).

The patent literature discloses IL-4 proteins and some muteins, but none directed to an IL-4 therapy with reduced side effects. Lee et al. U.S. Pat. No. 5,017,691 ("the '691 patent") is directed to mammalian proteins and muteins of human IL-4 which disclose both B-cell growth factor activity and T cell growth factor activity. It discloses nucleic acids coding for polypeptides exhibiting IL-4 activity, as well as the polypeptides themselves and methods for their production. Muteins to the wild-type IL-4 at amino acid positions are disclosed that retain their ability to stimulate both B- and T cell proliferation in vitro. However, nothing in Lee suggests any T cell selective IL-4 muteins, anticipated activation of EC's or the endothelial cell leakiness which accompanies administration of IL-4. Thus, IL-4 itself is not enabling as a therapeutic modality because of the dose-limiting toxicity.

U.S. Pat. No. 5,013,824 describes hIL-4 peptide derivatives comprising from 6 to 40 amino acids of the native hIL-4. Also disclosed are immunogens comprising conjugates of the peptides and carriers. Carriers include erythrocytes, bacteriophages, proteins, synthetic particles or any substance capable of eliciting antibody production against the conjugated peptide. No muteins of IL-4 are disclosed.

WO96/04306-A2 discloses single-muteins that are antagonists and partial agonists of hIL-2 and hIL-13. No data regarding IL-4 is disclosed. WO95/27052 discloses splice mutants of IL-2 and IL-4 containing exons 1, 2 and 4.

There exists a need for an improved IL-4 molecule which has reduced toxicity and is more generally tolerated.

SUMMARY OF THE INVENTION

The invention is directed to human IL-4 muteins numbered in accordance with wild-type IL-4 having T cell activating activity, but having reduced endothelial cell activating activity. In particular, human IL-4 muteins wherein the surface-exposed residues of the D helix of the wild-type IL-4 are mutated whereby the resulting mutein causes T cell proliferation, and causes reduced IL-6 secretion from HUVECs, relative to wild-type IL-4. This invention realizes a less toxic IL-4 mutein that allows greater therapeutic use of this interleukin.

Further, the invention is directed to IL-4 muteins having single, double and triple mutations represented by the designators R121A, R121D, R121E, R121F, R121H, R121I, R121K, R121N, R121P, R121T, R121W; Y124A, Y124Q, Y124R, Y124S, Y124T; Y124A/S125A, T13D/R121E; and R121T/E122F/Y124Q, when numbered in accordance with wild type IL-4 (His=1). The invention also includes polynucleotides coding for the muteins of the invention, vectors containing the polynucleotides, transformed host cells, pharmaceutical compositions comprising the muteins, and therapeutic methods of treatment.

The invention is also directed to a vector comprising the polynucleotide encoding a mutein of this invention, the vector directing the expression of a human IL-4 mutein having T cell activating activity but having reduced endothelial cell activating activity, the vector being capable of enabling transfection of a target organism and subsequent in vivo expression of said human IL-4 mutein coded for by said polynucleotide.

The invention is also directed to a method of selecting a human IL-4 mutein numbered in accordance with wild-type IL-4 having T cell activating activity but having reduced endothelial cell activating activity, comprising mutating the surface-exposed residues of the D helix of the wild-type IL-4 whereby the resulting mutein causes T cell proliferation, and causes reduced IL-6 secretion from HUVECs, relative to wild-type.

The invention is also directed to a method of treating a patient afflicted with an IL-4 treatable condition by administering a therapeutically effective amount of a human IL-4 mutein numbered in accordance with wild-type IL-4 having T cell activating activity but having reduced endothelial cell activating activity. This method is applicable wherein the IL-4 treatable condition is an autoimmune disorder, cancer, infectious disease, cartilage disorder, and psoriatic disorders.

BRIEF DESCRIPTION OF THE DRAWINGS

FIG. 1 is an amino acid sequence (SEQ ID NO: 1) of mature wild-type human IL-4 used in this study. Helices are underlined and labeled sequentially A, B, C, and D. Positions that, when mutated yielded cell-selective IL-4 agonists, are indicated in bold type.

FIG. 3A and B is a composite dose response curve for selective agonist muteins in the HUVEC IL-6 secretion assay. Panel A: ○, wild-type IL-4; ●, R121E; ▽, R121P; ▼, R121T/E122F/Y124Q. Panel B: ○, wild-type IL-4; ●, Y124Q; ▽, Y124R; ▼, Y124A/S125A.

FIG. 4A–F are individual dose response curves of selective agonist muteins in the HUVEC IL-6 secretion assay. Panel A: ○, wild-type IL-4; ●, R121E. Panel B: ○, wild-type IL-4; ●, R121P. Panel C: ○, wild-type IL-4; ●, Y124Q. Panel D: ○, wild-type IL-4; ●, Y124R. Panel E: ○, wild-type IL-4; ●, Y124A/S125A. Panel F: ○, wild-type IL-4; ●, R121T/E122F/Y124Q.

FIG. 5 is a composite dose-response curve for selective agonist muteins for the biological response of IL-4 muteins in 1° T cell proliferation assays. Panel A: ○, wild-type IL-4; ●, R121E; ▽, R121P; ▼, R121T/E122F/Y124Q. Panel B: ○, wild-type IL-4; ●, Y124Q; ▽, Y124R; ▼, Y124A/S125A.

FIG. 6 are individual dose response curves of the 1° T cell proliferation assay. Panel A: ○, wild-type IL-4; ●, R121E. Panel B: ○, wild-type IL-4; ●, R121P. Panel C: ○, wild-type IL-4; ●, Y124Q. Panel D: ○, wild-type IL-4; ●, Y124R. Panel E: ○, wild-type IL-4; ●, Y124A/S125A. Panel F: ○, wild-type IL-4; ●, R121T/E122F/Y124Q.

FIG. 7 are individual dose response curves showing the antagonism of IL-4-induced IL-6 secretion on HUVEC by the T cell-selective agonist IL-4 muteins R121E (●) and Y124Q (▽). The dose response of the IL-4 antagonist R121D/Y124D (○) is included as a control.

FIGS. 8A, 8B are individual dose response curves: Panel A shows the biological response of the R121D mutein in a 1° T cell proliferation assay (○=IL-4,●=R121D); Panel B shows the inability of R121D to induce IL-6 secretion on HUVEC (○=IL-4, ●=R121D).

FIG. 9A are the individual dose response curves for IL-4 (○) and the T cell-selective agonist muteins R121E (▽) and T13D/R121E (▲) in the 1° T cell proliferation assay.

FIG. 9B are individual dose response curves showing the antagonism of IL-4-induced IL-6 secretion on HUVEC by the T cell-selective IL-4 agonist muteins R121E (A) and T13D/R121E (A).

DESCRIPTION OF THE PREFERRED EMBODIMENTS

A. Background

Figure 2:
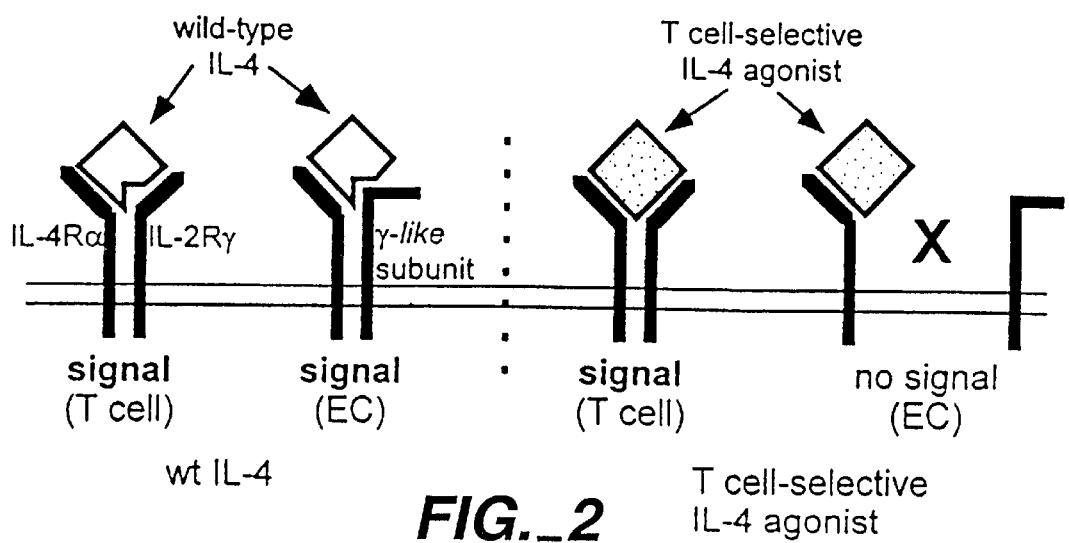
FIG. 2 is a graphical presentation of the T cell selective agonist concept.

IL-4 has been shown to mediate a variety of cellular responses in vitro, including various effects on B cells, T cells, and monocytes, as well as endothelial cells (Maher D W, Davis I, Boyd A W, Morstyn G: Human interleukin-4: an immunomodulator with potential therapeutic applications. *Prog Growth Factor Res* 3:43–56, 1991; Powrie F, Coffman R L: Cytokine regulation of T cell function: potential for therapeutic intervention. *Immunol Today* 14:270–4, 1993). In particular, upregulation of vascular cell adhesion molecule-1 (VCAM-1; (Swerlick R A, Lee K H, Li L J, Sepp N T, Caughman S W, Lawley T J: Regulation of vascular cell adhesion molecule 1 on human dermal microvascular endothelial cells. *J Immunol* 149:698–705, 1992)) and induction of IL-6 (Colotta F, Sironi M, Borre A, Luini W, Maddalena F, Mantovani A: Interleukin 4 amplifies monocyte chemotactic protein and interleukin 6 production by endothelial cells. *Cytokine* 4:24–8, 1992) and monocyte chemoattractant protein-1 (MCP-1; Colotta F, Sironi M, Borre A, Luini W, Maddalena F, Mantovani A: Interleukin 4 amplifies monocyte chemotactic protein and interleukin 6 production by endothelial cells. *Cytokine* 4:24–8, 1992; Rollins B J, Pober J S: Interleukin-4 induces the synthesis and secretion of MCP-1/JE by human endothelial cells. *Am J Pathol* 138:1315–9, 1991)) are direct effects of IL-4 on cultured endothelial cells; the upregulation of VCAM-1 is correlated with the increased adhesion of lymphocytes both in vitro (Carlos T M, Schwartz B R, Kovach N L, Yee E, Rosa M, Osborn L, Chi-Rosso G, Newman B, Lobb R, Rosso M, et al.: Vascular cell adhesion molecule-1 mediates lymphocyte adherence to cytokine-activated cultured human endothelial cells. *Blood* 76:965–70, 1990; Thornhill M H, Wellicome S M, Mahiouz D L, Lanchbury J S, Kyan-Aung U, Haskard D O: Tumor necrosis factor combines with IL-4 or IFN-gamma to selectively enhance endothelial cell adhesiveness for T cells. The contribution of vascular cell adhesion molecule-1-dependent and -independent binding mechanisms. *J Immunol* 146:592–8, 1991) and in vivo (Briscoe D M, Cotran R S, Pober J S: Effects of tumor necrosis factor, lipopolysaccharide, and IL-4 on the expression of vascular cell adhesion molecule-1 in vivo. Correlation with CD3+ T cell infiltration. *J Immunol* 149:2954–60, 1992).

The IL-4 mutein IL-4/Y124D (substitution of Aspartic acid for Tyrosine at position 124) is a T cell antagonist, (Kruse N, Tony H P, Sebald W: Conversion of human interleukin-4 into a high affinity antagonist by a single amino acid replacement. *Embo J* 11:3237–44, 1992). In vivo experiments performed by the inventors have demonstrated that IL-4Y124D exhibits acute toxicity similar to that of wild-type IL-4 in monkeys, a previously undescribed observation. The cellular events associated with both wild-type IL-4- and IL-4/Y124D-mediated toxicity include upregulation of VCAM-1, upregulation of MCP-1 in serum, increases in circulating monocytes together with a concomitant decrease in circulating lymphocytes, and an increase in hematocrit. Similar cellular trafficking has been observed in clinical trials using IL-4 in humans (Wong H L, Lotze M T, Wahl L M, Wahl S M: Administration of recombinant IL-4 to humans regulates gene expression, phenotype, and function in circulating monocytes. *J Immunol* 148:2118–25, 1992). Due to its properties as an antagonist of T cells, these results suggest that the toxicities demonstrated by IL-4Y124D are due to agonist activities on and are mediated through cells other than T cells. The observed in vivo toxicities using IL-4/Y124D and the known effects of IL-4 on endothelial cells are consistent with the mechanism that in vivo IL-4 toxicity is mediated through direct effects of IL-4 on the vascular endothelium.

Through these (and related) investigations, the inventors have discovered that a new IL-4 receptor may exist on endothelial cells ("EC"). This possibility led to efforts to synthesize IL-4 muteins that would selectively activate T cells, but not EC. While T cells express an IL-4 receptor composed of IL-4Rα and IL-2Rγ subunits, the inventors have discovered that human umbilical vein endothelial cells (HUVEC), express IL-4Rα but not IL-2Rγ. Crosslinking studies have shown that two receptor chains are expressed at the cell surface of HUVEC: the molecular weight of one is consistent with IL-4Rα, and a second, lower molecular weight chain. These results suggest that a novel IL-4 receptor component similar in function to IL-2Rγ, but differing in sequence, is expressed on HUVECs. The differences in the specific molecular structures between these two receptors were thus exploited to generate an IL-4 variant that is selective for one receptor over the other (e.g., a T cell selective agonist).

FIG. 2 demonstrates graphically the selective agonist concept. It shows the T cell IL-4 receptor comprising the IL-4Rα/IL-2Rγ subunit, and an Endothelial cell IL-4 receptor comprising the IL-4Rα/γ-like receptor subunit. Although depicted here together for purposes of illustration only, the two receptors for IL-4 are expressed on different cell types. The T cell receptor is composed of IL-4Rα and IL-2Rγ; IL-4 binding induces receptor heterodimer formation that results in cellular signalling. IL-4 induced receptor heterodimer formation occurs in a similar manner on EC's, except that the receptor for IL-4 is composed of IL-4Rα and a γ-like receptor component. The γ-like receptor component is different from IL-2Rγ. T cell-selective IL-4 agonists are those variants of IL-4 that retain their ability to interact with the T cell receptor IL-4Rα/IL-2Rγ, but are unable to induce heterodimerization, and thus signalling, of the non-T cell receptor IL-4Rα/γ-like subunit. Such T cell-selective IL-4 agonists retain their ability to interact with IL-4Rα; it is their ability to discriminate between IL-2Rγ and the γ-like subunit that gives them their cell-selective activation properties.

The two components of the T cell receptor, IL-4-Rα and IL-2Rγ, contact different regions of the IL-4 molecule, and therefor the inventors have focussed on a small region of IL-4 to modify. Hypothesizing that the novel receptor subunit would contact the same region of IL-4 as does IL-2Rγ, the inventors made a number of substitutions in the D-Helix, particularly residues 121, 124 and 125.

The D-helix has been implicated in interactions with both IL-2Rγ and with the putative novel receptor on HUVEC (specifically, the IL-4 mutein R121D/Y124D is a HUVEC antagonist). Muteins containing modifications to the D-helix of IL-4 (residues 110 to 126; His=1) were screened for their ability to stimulate either T cell proliferation or human umbilical vein endothelial cell (HUVEC) secretion of IL-6. Muteins that induced a differential response on T cells relative to HUVEC were further characterized through further mutagenesis.

An initial scan of the D helix was undertaken to determine the potential areas of interaction. Additionally, alanine scanning substitutions of the AB loop were also generated, as this region is suggested to be involved in the interaction of the cytokine ligand and the D-helix interacting receptor subunit. In particular, surface-exposed residues Glu-110, Asn-111, Glu-114, Arg-115, Lys-117, Thr-118, Arg-121, Glu-122, Tyr-124, Ser-125, and Lys-126 were targeted for investigation and are preferred targets for mutation analysis. Sites 118–126 are more preferred, and sites 121–125 are most preferred. Comparisons between IL-2, IL-4, IL-7 and IL-15 in this region also identify differences between IL-4 and IL-2, IL-7 and IL-15, possibly suggesting specific residues responsible for the HUVEC receptor interaction. Specific substitutions derived from an alignment between IL-2 and IL-4 were introduced into IL-4. These included: Arg-115 to Phe; Lys-117 to Asn; Glu-122 to Phe; Lys-126 to Ile; and three simultaneous changes Arg-121 to Thr, Glu-122 to Phe, and Tyr-124 to Gln.

Mutations were introduced using site-directed mutagenesis on wild-type human IL-4 cDNA. Correct clones were subcloned to an expression vector suitable for expression in a heterologous system (e.g., *E. coli*, baculovirus, or CHO cells). Purified proteins were tested in T cell proliferation and HUVEC cytokine secretion assays (IL-6). Different responses generated by individual muteins between these assays, either in $ECS_{50}$ or maximal response (plateau) indicate mutations that effect these activities. Specifically, muteins that stimulate a relatively stronger response in the T cell assay (vs. wild-type IL-4) as compared to the response on HUVEC (vs. wild-type IL-4) will suggest positions that are more important to the interaction of IL-4 with IL-2Rγ than the interaction of IL-4 with the novel HUVEC IL-4 receptor. Further analysis and mutagenesis (e.g. combinatorial changes, substitution with all amino acids) of the identified positions will produce an IL-4 mutein with selective agonist properties for the T cell IL-4 receptor. This protein will also be a selective antagonist for IL-4-induced HUVEC responses.

B. Definitions

Described herein are novel muteins and a mechanism for deriving novel IL-4 muteins with selective agonist properties on T cells and reduced toxicity. A similar strategy may be used to identify a T cell-selective antagonist.

As used herein, "wild type IL-4" means IL-4, whether native or recombinant, having the 129 normally occurring amino acid sequence of native human IL-4, as shown, e.g., in FIG. 1.

As used herein, "IL-4 mutein" means a polypeptide wherein specific substitutions to the human mature interleukin-4 protein have been made. Specifically disclosed herein, the arginine residue (R) at position 121 ("Arg-121"), when numbered in accordance with wild type IL-4, is substituted with alanine (A), aspartate (D), glutamate (E), phenylalanine (F), histidine (H), isoleucine (I), lysine (K), asparagine (N) proline (P), threonine (T) or tryptophan (W); or the glutamate (E) residue at position 122 is substituted with phenylalanine (F); or the tyrosine residue at position 124 is substituted with alanine (A), glutamine (Q), arginine (R) serine (S) or threonine (T); or the serine (S) residue at position 125 is substituted with alanine (A). Our most preferred IL-4 muteins have an amino acid sequence identical to wild type IL-4 at the other, non-substituted residues. However, the IL-4 muteins of this invention may also be characterized by amino acid insertions, deletions, substitutions and modifications at one or more sites in or at the other residues of the native IL-4 polypeptide chain. In accordance with this invention any such insertions, deletions, substitutions and modifications result in an IL-4 mutein that retains a T cell-selective activity while having reduced ability to activate endothelial cells.

We prefer conservative modifications and substitutions at other positions of IL-4 (i.e., those that have a minimal effect on the secondary or tertiary structure of the mutein). Such conservative substitutions include those described by Dayhoff in *The Atlas of Protein Sequence and Structure* 5 (1978), and by Argos in EMBO J., 8:779–785 (1989). For example, amino acids belonging to one of the following groups represent conservative changes:

ala, pro, gly, gln, asn, ser, thr;

cys, ser, tyr, thr;

val, ile, leu, met, ala, phe;

lys, arg, his;

phe, tyr, trp, his; and asp, glu.

We also prefer modifications or substitutions that do not introduce sites for additional intermolecular crosslinking or incorrect disulfide bond formation. For example, IL-4 is known to have six cys residues, at wild-type positions 3, 24, 46, 65, 99 and 127.

By "numbered in accordance with wild type IL-4" we mean identifying a chosen amino acid with reference to the position at which that amino acid normally occurs in wild type IL-4. Where insertions or deletions are made to the IL-4 mutein, one of skill in the art will appreciate that the ser (S) normally occuring at position 125, when numbered in accordance with wild type IL-4, may be shifted in position in the mutein. However, the location of the shifted ser (S) can be readily determined by inspection and correlation of the flanking amino acids with those flanking ser in wild type IL-4.

The IL-4 muteins of the present invention can be produced by any suitable method known in the art. Such methods include constructing a DNA sequence encoding the IL-4 muteins of this invention and expressing those sequences in a suitably transformed host. This method will produce recombinant muteins of this invention. However, the muteins of this invention may also be produced, albeit less preferably, by chemical synthesis or a combination of chemical synthesis and recombinant DNA technology.

In one embodiment of a recombinant method for producing a mutein of this invention, a DNA sequence is constructed by isolating or synthesizing a DNA sequence encoding the wild type IL-4 and then changing the codon for arg121 to a codon for alanine (A), aspartate (D), glutamate (E), phenylalanine (F), histidine (H), isoleucine (I), lysine (K), asparagine (N) proline (P), threonine (T) or tryptophan (W) by site-specific mutagenesis. This technique is well known. See, e.g., Mark et al., "Site-specific Mutagenesis Of The Human Fibroblast Interferon Gene", *Proc. Natl. Acad. Sci. USA* 81, pp. 5662–66 (1984); U.S. Pat. No. 4,588,585, incorporated herein by reference.

Another method of constructing a DNA sequence encoding the IL-4 muteins of this invention would be chemical synthesis. For example, a gene which encodes the desired IL-4 mutein may be synthesized by chemical means using an oligonucleotide synthesizer. Such oligonucleotides are designed based on the amino acid sequence of the desired IL-4 mutein, and preferably selecting those codons that are favored in the host cell in which the recombinant mutein will be produced. In this regard, it is well recognized that the genetic code is degenerate—that an amino acid may be coded for by more than one codon. For example, phe (F) is coded for by two codons, TTC or TTT, tyr (Y) is coded for by TAC or TAT and his (H) is coded for by CAC or CAT. Trp (W) is coded for by a single codon, TGG. Accordingly, it will be appreciated that for a given DNA sequence encoding a particular IL-4 mutein, there will be many DNA degenerate sequences that will code for that IL-4 mutein. For example, it will be appreciated that in addition to the preferred DNA sequence for mutein R121E shown in SEQ ID NO:3, there will be many degenerate DNA sequences that code for the IL-4 mutein shown. These degenerate DNA sequences are considered within the scope of this invention. Therefore, "degenerate variants thereof" in the context of this invention means all DNA sequences that code for a particular mutein.

The DNA sequence encoding the IL-4 mutein of this invention, whether prepared by site directed mutagenesis, synthesis or other methods, may or may not also include DNA sequences that encode a signal sequence. Such signal sequence, if present, should be one recognized by the cell chosen for expression of the IL-4 mutein. It may be prokaryotic, eukaryotic or a combination of the two. It may also be the signal sequence of native IL-4. The inclusion of a signal sequence depends on whether it is desired to secrete the IL-4 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-4 signal sequence be used.

Standard methods may be applied to synthesize a gene encoding an IL-4 mutein according to this invention. For example, the complete amino acid sequence may be used to construct a back-translated gene. A DNA oligomer containing a nucleotide sequence coding for IL-4 mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis or another method), the DNA sequences encoding an IL-4 mutein of this invention will be inserted into an expression vector and operatively linked to an expression control sequence appropriate for expression of the IL-4 mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E.coli,* including col E1, pCR1, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2$\mu$ plasmid and derivatives thereof Useful vectors for insect cells include pVL 941. We prefer pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685–98 (1986).

In addition, any of a wide variety of expression control sequences may be used in these vectors. Such useful expression control sequences include the expression control sequences associated with structural genes of the foregoing expression vectors. Examples of useful expression control seguences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast α-mating system, the polyhedron promotor of Baculovirus, and other sequences known to control the expression of genes of prokaryotic or eukaryotic cells or their viruses, and various combinations thereof.

Any suitable host may be used to produce the IL-4 muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E.coli,* Pseudomonas, Bacillus, Streptomyces, fungi, yeast, insect cells such as *Spodoptera frugiperda* (Sf9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, we prefer CHO cells and COS 7 cells in cultures and particularly the CHO cell line CHO (D HFR-).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IL-4 muteins to be amplified in copy number. Such amplifiable vectors are well known in the art. They include, for example, vectors able to be amplified by DHFR amplification (see, e.g., Kaufman, U.S. Pat. No. 4,470,461, Kaufinan and Sharp, "Construction Of A Modular Dihydrafolate Reductase cDNA Gene: Analysis Of Signals Utilized For Efficient Expression", Mol. Cell. Biol., 2, pp. 1304–19 (1982)) or glutamine synthetase ("GS") amplification (see, e.g., U.S. Pat. No. 5,122,464 and European published application 338,841).

In selecting an expression control sequence, a variety of factors should also be considered. These include, for example, the relative strength of the sequence, its controllability, and its compatibility with the actual DNA sequence encoding the IL-4 mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters, one of skill in the art may select various vector/expression control sequence/host combinations that will express the desired DNA seguences on fermentation or in large scale animal culture, for example, using CHO cells or COS 7 cells.

The IL-4 muteins obtained according to the present invention may be glycosylated or unglycosylated depending on the host organism used to produce the mutein. If bacteria are chosen as the host then the IL-4 mutein produced will be unglycosylated. Eukaryotic cells, on the other hand, will glycosylate the IL-4 muteins, although perhaps not in the same way as native IL-4 is glycosylated.

The IL-4 mutein produced by the transformed host can be purified according to any suitable method. Various methods are known for purifying IL-4. See, e.g., U.S. Pat. Nos. 5,013,824; 5,017,691; and WO9604306-A2. We prefer immunoaffinity purification. See, e.g., Okamura et al., "Human Fibroblastoid Interferon: Immunosorbent Column Chromatography And N-Terminal Amino Acid Sequence", *Biochem.,* 19, pp. 3831–35 (1980).

The biological activity of the IL-4 muteins of this invention can be assayed by any suitable method known in the art. Such assays include antibody neutralization of antiviral activity, induction of protein kinase, oligoadenylate 2,5-A synthetase or phosphodieiterase activities, as described in EP-B1-141313. Such assays also include immunomodulatory assays (see, e.g., U.S. Pat. No. 4,753,795), growth inhibition assays, T cell proliferation, induction of IL-6

(MCP-1 or VCAM-1) on EC and measurement of binding to cells that express interleukin-4 receptors. See also Spits H, Yssel H, Takebe Y, et al., Recombinant Interleukin-4 Promotes the Growth of Human T Cells, J. IMMUNOL 139:1142–47 (1987).

The IL-4 mutein of this invention will be administered at a dose approximately paralleling that or greater than employed in therapy with wild type native or recombinant IL-4. An effective amount of the IL-4 mutein is preferably administered. An "effective amount" means an amount capable of preventing or lessening the severity or spread of the condition or indication being treated. It will be apparent to those of skill in the art that the effective amount of IL-4 mutein will depend, inter alia, upon the disease, the dose, the administration schedule of the IL-4 mutein, whether the IL-4 mutein is administered alone or in conjunction with other therapeutic agents, the serum half-life of the composition, and the general health of the patient.

The IL-4 mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer 2% HSA/PBS at pH 7.0.

The IL-4 muteins of the present invention can be formulated into pharmaceutical compositions by well known methods. See, e.g., Remington's Pharmacautical Science by E. W. Martin, hereby incorporated by reference, describes suitable formulations. The pharmaceutical composition of the IL-4 mutein may be formulated in a variety of forms, including liquid, gel, lyophilized, or any other suitable form. The preferred form will depend upon the particular indication being treated and will be apparent to one of skill in the art.

The IL-4 mutein pharmaceutical composition may be administered orally, by aerosol, intravenously, intramuscularly, intraperitoneally, intradermally or subcutaneously or in any other acceptable manner. The preferred mode of administration will depend upon the particular indication being treated and will be apparent to one of skill in the art. The pharmaceutical composition of the IL-4 mutein may be administered in conjunction with other therapeutic agents. These agents may be incorporated as part of the same pharmaceutical composition or may be administered separately from the IL-4 mutein, either concurrently or in accordance with any other acceptable treatment schedule. In addition, the IL-4 mutein pharmaceutical composition may be used as an adjunct to other therapies.

Accordingly, this invention provides compositions and methods for treating immune disorders, cancers or tumors, abnormal cell growth, or for immunomodulation in any suitable animal, preferably a mammal, most preferably human. As previously noted in the Background section, IL-4 has many effects. Some of these are stimulation of T cell proliferation, T-helper cell differentiation, induction of human B-cell activation and proliferation, and lymphokine-directed immunoglobulin class switching. Effects on the lymphoid system include increasing the expression of MHC class II antigen (Noelle, R., et al., Increased Expression of Ia Antigens on resting B cells: a New Role for B Cell Growth Factor, *PNAS USA*, 81:6149–53 (1984)), and CD 23 on B cells (Kikutani, H., et al., Molecular Structure of Human Lymphocyte Receptor for Immunoglobulin, *Cell* 47:657–61 (1986)). T-helper cell type 1 (Th1) and type 2 (Th2) are involved in the immune response. Stimulated Th2 cells secrete IL-4 and block Th1 progression. Thus, any Th1-implicated disease is amenable to treatment by IL-4 or analogs thereof.

Also contemplated is use of the DNA sequences encoding the IL-4 muteins of this invention in gene therapy applications. Gene therapy applications contemplated include treatment of those diseases in which IL-4 is expected to provide an effective therapy due to its immunomodulatory activity, e.g., Multiple Sclerosis (MS), Insulin-dependent Diabetes Mellitus (IDDM), Rheumatoid Arthritis (RA), Systemic Lupus Erythematosus (SLE), uveitis, orchitis, primary biliary cirrhosis, malaria, leprosy, Lyme Disease, contact dermatitis, psoriasis, B cell lymphoma, acute lymphoblastic leukemia, non-Hodgkins lymphoma, cancer, osteoarthritis and diseases that are otherwise responsive to IL-4 or infectious agents sensitive to IL-4-mediated immune response.

Local delivery of IL-4 muteins using gene therapy may provide the therapeutic agent to the target area. Both in vitro and in vivo gene therapy methodologies are contemplated. Several methods for transferring potentially therapeutic genes to defined cell populations are known. See, e.g., Mulligan, "The Basic Science Of Gene Therapy", *Science*, 260: 926–31 (1993). These methods include:

1) Direct gene transfer. See, e.g., Wolff et al., "Direct Gene transfer Into Mouse Muscle In Vivo", *Science*, 247:1465–68 (1990);

2) Liposome-mediated DNA transfer. See, e.g., Caplen at al., "Liposome-mediated CFTR Gene Transfer To The Nasal Epithelium Of Patients With Cystic Fibrosis", *Nature Med.* 3: 39–46 (1995); Crystal, "The Gene As A Drug", Nature Med. 1:15–17 (1995); Gao and Huang, "A Novel Cationic Liposome Reagent For Efficient Transfection Of Mammalian Cells", *Biochem. Biophys. Res. Comm.*, 179:280–85 (1991);

3) Retrovirus-mediated DNA transfer. See, e.g., Kay et al., "In Vivo Gene Therapy Of Hemophilia B: Sustained Partial Correction In Factor IX-Deficient Dogs", *Science*, 262:117–19 (1993); Anderson, "Human Gene Therapy", *Science*, 256:808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy", *Gene Therapy*, 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et al., supra, p. 377.

In a preferred embodiment, the IL-4 mutein-encoding DNA of this invention is used in gene therapy for autoimmune diseases such as MS, IDDM, and RA, infectious diseases such as Lyme Disease and Leprosy, cancers, such as non-Hodgkins lymphoma and ALL, cartiledgenous disorders such as osteoarthritis, and psoriatic conditions, such as psoriasis.

According to this embodiment, gene therapy with DNA encoding the IL-4 muteins of this invention is provided to a patient in need thereof, concurrent with, or immediately after diagnosis.

This approach takes advantage of the selective activity of the IL-4 muteins of this invention to prevent undesired autoimmune stimulation. The skilled artisan will appreciate that any suitable gene therapy vector containing IL-4 mutein DNA may be used in accordance with this embodiment. The techniques for constructing such a vector are known. See, e.g., Ohno et al., supra, p. 784; Chang et al., supra, p. 522. Introduction of the IL-4 mutein DNA-containing vector to the target site may be accomplished using known techniques, e.g., as described in Ohno et al., supra, p. 784.

In order that this invention may be better understood, the following examples are set forth. These examples are for the purpose of illustration only, and are not to be construed as limiting the scope of the invention in any manner.

EXAMPLES

Generally

The amino acid sequence of mature human IL-4 used in this study is shown below. Amino acids at which substitutions yielded T cell selective agonists are indicated in bold type:

(HUVEC) were used to assess activity through the alternate IL-4 receptor (IL-4Rα/γ-like receptor component).

Example 1

Production of

| | | |
|---|---|---|
| R121A: | CTAAAGACGA TCATGGCTGA GAAATATT | (SEQ ID NO:24) |
| R121D: | GCTAAAGACG ATCATGGACG AGAAATATTC | (SEQ ID NO:25) |
| R121E: | GCTAAAGACG ATCATGG<u>AA</u>G AGAAATATTC | (SEQ ID NO:26) |
| R121F: | CTAAAGACGA TCATGTTTGA GAAATATT | (SEQ ID NO:27) |
| R121H: | CTAAAGACGA TCATGCACGA GAAATATT | (SEQ ID NO:28) |
| R121I: | CTAAAGACGA TCATGATAGA GAAATATT | (SEQ ID NO:29) |
| R121K: | CTAAAGACGA TCATGAAAGA GAAATATT | (SEQ ID NO:30) |
| R121N: | CTAAAGACGA TCATGAACGA GAAATATT | (SEQ ID NO:31) |
| R121P: | GCTAAAGACG ATCATG<u>CC</u>AG AGAAATATTC | (SEQ ID NO:32) |
| R121T: | CTAAAGACGA TCATGACTGA GAAATATT | (SEQ ID NO:33) |
| R121W: | CTAAAGACGA TCATGTGGGA GAAATATT | (SEQ ID NO:34) |
| Y124A: | ATCATGAGAG AGAAAGCATC AAAGTGTT | (SEQ ID NO:35) |
| Y124Q: | ATCATGAGAG AGAAA<u>CAA</u>TC AAAGTGTT | (SEQ ID NO:36) |
| Y124R: | ATCATGAGAG AGAAA<u>CGA</u>TC AAAGTGTT | (SEQ ID NO:37) |
| Y124S: | ATCATGAGAG AGAAATCATC AAAGTGTT | (SEQ ID NO:38) |
| Y124T: | ATCATGAGAG AGAAAACATC AAAGTGTT | (SEQ ID NO:39) |
| Y124A/S125A: | CGATCATGAG AGAGAAA<u>GCT</u> GCTAAGTGTT CGA | (SEQ ID NO:40) |
| T13D: | CAGGAGATCA TCAAA<u>GA</u>TTT GAACAGCC | (SEQ ID NO:41) |
| R121T/E122F/Y124Q: | GCTAAAGACG ATCATG<u>ACCT</u> <u>TC</u>AAACAGTC AAAG | (SEQ ID NO:42) |

Regions of mutated nucleotides are underlined. Primers were phosphorylated using T4 polynucleotide kinase (New England Biolabs, Beverly, Mass.) using the manufacturer's protocol. After annealing of the primer to the U-DNA template and extension with T7 DNA polymerase (Bio-Rad Laboratories, Hercules, Calif.), cells of the *E. coli* strain DH5α™ (GibcoBRL, Gaithersburg, Md.) were transformed with 5 µl of reaction mixture and plated in LB medium containing 0.7% agar. After incubation at 37° C., plaques were expanded by picking a single plaque and transferring to 2 mls of LB media and grown overnight at 37° C. Single strand DNA was isolated using an M13 purification kit (Qiagen, Inc., Chatsworth, Calif.) per manufacturer's protocol, and clones containing the desired mutation were identified by sequencing the single stranded DNA using the Sequenase® sequencing kit (Amersham Life Sciences, Arlington Heights, Ill.) per manufacturer's protocol. IL-4 mutein cDNA from Replicative Form DNA corresponding to plaques containing the correct mutated sequence was isolated using Bam HI and Xba I, and subcloned to the plasmid vector pFastBac™ 1 (GibcoBRL, Gaithersburg, Md.). After subcloning, recombininant baculovirus DNA (hereafter referred to as Bacmid) was generated by transforming pFastBac™ 1 containing the mutein cDNA to the *E. coli* strain DH10Bac™ (GibcoBRL, Gaithersburg, Md.) as described by the manufacturer. Muteins were expressed in *Spodoptera frugiperda* (Sf) 9 cells using the Bac-to-Bac (GibcoBRL, Gaithersburg, Md.) baculovirus expression system. All insect cell incubations occurred at 28° C. Briefly, 2 ml cultures of Sf 9 cells were transfected with 5 82 l of recombinant Bacmid using CellFECTIN (GibcoBRL, Gaithersburg, Md.). The supernatant was harvested 60 hours post-transfection, and used to infect a 100–200 ml culture of $1 \times 10^6$ Sf 9 cells/ml in Grace's media (GibcoBRL, Gaithersburg, Md.). Per manufacturer's protocol, the supernatants were harvested 48–60 hrs post-infection by centrifugation at 5000 rpm for 10 minutes in a Sorvall® RC-5B centrifuge using a GSA rotor (Dupont Instrument Co., Willmington, Del.) and assayed for virus titre (typically, >$1 \times 10^8$ plaque forming units/ml was obtained). For protein production, $2-3 \times 10^6$ Sf9 cells/ml in 500 mls of SF900 II media (GibcoBRL, Gaithersburg, Md.) were infected at a multiplicity of infection between 4–10 and the supernatant was harvested 60–72 hrs post-infection by centrifugation at 5000 rpm for 10 minutes in a Sorvall® RC-5B centrifuge using a GSA rotor (Dupont Instrument Co., Willmington, Del.) and filtered through a sterile 0.2 µM filter unit.

Example 2

Purification of Muteins

Anti-human IL-4 monoclonal antibodies C400.1 and C400.17 were generated using standard protocols from mice using recombinant human IL-4 (Genzyme Diagnostics, Cambridge, Mass.) as immunogen, were produced as ascites fluid, purified, and coupled to CNBr-activated Sepharose (Pharmacia, Uppsala, Sweden) as per manufacturer's protocol. Sf 9 cell supernatants generated from infection of Sf 9 cells by recombinant baculovirus containing the respective IL-4 mutein were loaded onto a 1 ml column of IL-4 affinity matrix, washed with 100 mM NaHCO$_3$, 500 mM NaCl, pH 8.3, washed with water to remove salt, and eluted with 8 column volumes of 100 mM Glycine, pH 3.0. Fractions were collected in siliconized vials containing 0.1 volume 1 M Tris, pH 8.0. Mutein protein was further purified by reverse phase chromatography using a Dynamax®-300 Å C$_{18}$ column (Rainin Instrument Co., Woburn, Mass.) with a 0–100% gradient of Buffer A to B (Buffer A, water; Buffer B, acetonitrile, 0.1% trifluoroacetic acid). Fractions were evaluated by SDS-PAGE, and mutein containing fractions were lyophilized for storage, and resuspended in sterile phosphate-buffered saline for assays. Mutein so purified was typically a single band as observed by SDS-PAGE (silver stain), and was quantitated by amino acid analysis (accuracy typically >90%).

Example 3

1° T Cell Proliferation Assay

Primary T cells were obtained from fresh blood from normal donors and purified by centrifugation using Ficoll-Paque® Plus (Pharmacia, Upsalla, Sweden) essentially as described by Kruse, N., Tony, H. P. and Sebald, W. "Conversion of human interleukin-4 into a high affinity antagonist by a single amino acid replacement", *Embo J.* 11: 3237–44 (1992). The purified peripheral blood mononuclear cells were incubated for 7 days with 10 μg/ml phytohemagglutinin (Sigma Chemical Co., St. Louis, Mo.), harvested by centrifugation, and washed in RPMI 1640 media (GibcoBRL, Gaithersburg, Md.). $5 \times 10^4$ activated T cells/well (PHA-blasts) were incubated with varying amounts of IL-4 or mutein in RPMI 1640 media containing 10% fetal bovine serum, 10 mM HEPES, pH 7.5, 2 mM L-glutamine, 100 units/ml penicillin G, and 100 μg/ml streptomycin sulphate in 96 well plates for 72 hrs at 37° C., pulsed with 1 μCi $^3$H-thymidine (DuPont NEN®, Boston, Mass.)/well for 6 hrs, harvested, and radioactivity was measured in a TopCount™ scintillation counter (Packard Instrument Co., Meriden, Conn.).

Example 4

HUVEC IL-6 Secretion Assay

Human umbilical vein endothelial cells (HUVEC) were obtained from Clonetics® Corp. (San Diego, Calif.), and maintained as per supplier's protocols. Cells (passage 3 to 6) were harvested by incubation with Trypsin/EDTA, washed, and plated at subconfluent densities in 48-well plates in EGM® media (Clonetics® Corp., San Diego, Calif.) containing bovine brain extract (BBE; Clonetics® Corp., San Diego, Calif.). At confluency (3–4 days at 37° C.), the media was removed and replaced with EGM® media without BBE. 24 hours later, varying concentrations of IL-4 or mutein was added to the cells in fresh EGM® without BBE, and allowed to incubate an additional 24 hrs. Supernatants were harvested and the concentration of IL-6 was analyzed using a human IL-6 ELISA. The conditions were identical except for antagonist assays, varying concentrations of mutein were added to a constant concentration of 100 pM IL-4. Briefly, 96-well Immunolon® 2 plates (Dynatech Laboratories, Inc., Chantilly, Va.) were coated with 5 μg/ml anti-human IL-6 MAb Cat#1618–01 (Genzyme Diagnostics, Cambridge, Mass.) overnight at 4° C. Human IL-6 standard (Genzyme Diagnostics, Cambridge, Mass.) or samples were titrated in duplicate and incubated with the coated plate; after washes, secondary antibody rabbit anti-human IL-6 PAb (Caltag Laboratories, South San Francisco, Calif., Cat#PS-37) at a 1:1000 dilution was added. The presence of bound rabbit anti-IL-6 PAb was detected using alkaline phosphatase-coupled donkey anti-rabbit Ig PAb (Jackson ImmunoResearch Laboratories, Inc., West Grove, Pa., Cat#711–055–152) diluted 1:2000, and developed using pNPP (Sigma Chemical Co., St. Louis, Mo., Cat#N2770 or N1891). Absorbance was read at 405 nm using a Vmax™ kinetic microplate reader (Molecular Devices Corp., Menlo Park, Calif.).

Example 5

Activities of Muteins

Table 1 summarizes the results of the muteins in the two assays described above. "$EC_{50}$, pM" is the effective concentration that produces a 50% maximal response measured in the concentration picomoles/liter. Activity is a function of both potency ($EC_{50}$) and maximal response ($R_{max}$). Cell-selective muteins exhibited differential activity of either a relative reduction in $R_{max}$ and/or a relative reduction in potency (increase in $EC_{50}$) in the HUVEC assay vs. the T cell assay. "$R_{max}$, % wt" is the maximal response measured relative to wild-type IL-4. By definition, wild-type IL-4 gives 100% response. All muteins were active in the T cell proliferation assay. Muteins R121D, R121E, R121P, and R121T/E122F/Y124Q were more potent than wild-type IL-4 in this assay, although mutein R121T/E122F/Y124Q had a reduced maximal response. Muteins Y124Q, Y124R, and Y124A/S125A had 2–3-fold increased $EC_{50}$ values than wild-type, as well as a reduced maximal response. However, they appear to retain a significant proportion of IL-4 activity on T cells. Muteins R121E, Y124Q and R121T/E122F/Y124Q had no measurable activity in the HUVEC assay, making them clearly T cell-selective, and thus selective for the IL-4 receptor expressed on T cells (IL-4Rα/IL-2Rγ). These muteins are IL-4 antagonists on endothelial cells because, although they interact normally with IL-4Rα, they do not activate the complex IL-4Rα/γ-like subunit. The muteins R121P and Y124R show activity in the HUVEC assay, but their $EC_{50}$ values are increased between 50–150-fold, and have reduced maximal responses relative to their ability to stimulate T cells. Although these two proteins do not appear to be absolutely T cell-selective, they are preferential for their activation of the T cell IL-4 receptor over the HUVEC IL-4 receptor.

TABLE 1

Muteins with preferential activity on T cells vs. endothelial cells

| | 1° T cell proliferation | | HUVEC, IL-6 secretion | |
|---|---|---|---|---|
| Mutein | $EC_{50}$, pM | $R_{max}$, % wt | $EC_{50}$, pM | $R_{max}$, % wt |
| wildtype IL-4 | 150 | 100 | 20 | 100 |
| R121A | 150 | 100 | 20 | 65 |
| R121D | 100 | 40 | — | 0 |
| R121E | 65 | 100 | — | 0 |
| R121F | 150 | 100 | 20 | 60 |
| R121H | 150 | 80 | 40 | 70 |
| R121I | 100 | 100 | 40 | 50 |
| R121K | 150 | 100 | 100 | 75 |
| R121N | 150 | 100 | 35 | 50 |
| R121P | 100 | 100 | 650 | 45 |
| R121T | 150 | 100 | 20 | 75 |
| R121W | 150 | 100 | 80 | 35 |
| Y124A | 150 | 50 | 65 | 50 |
| Y124Q | 250 | 15 | 200 | 25 |
| Y124R | 750 | 30 | 250 | 25 |
| Y124S | 425 | 15 | 350 | 20 |
| Y124T | 300 | 15 | 350 | 35 |
| Y124A/S125A | 600 | 60 | 200 | 30 |
| R121T/E122F/Y124Q | 15 | 13 | — | 0 |

Example 6

Biological Response of IL-4 Muteins in HUVEC Assays

FIGS. 2A and B are a series of dose-response plots of HUVEC IL-6 secretion by the T cell-selective agonists relative to wild-type. IL-4 was included as an internal control on each plate used to assay mutein activity; a representative curve is shown. FIG. 4A is the dose-response curve for R121E versus wild-type IL-4. Similarly, FIG. 4B–F are the dose-response curves for R121P, Y124Q, Y124R, Y124A/S125A, and R121T/E122F/Y124Q, respectively, versus wild-type IL-4. Activities have been normalized relative to the IL-4 control responses. Muteins R121E, Y124Q, and R121T/E122F/Y124Q demonstrate no activity in this assay. Muteins R121P and Y124R, though showing partial agonist activity in this assay, are relatively less potent to wild-type IL-4 than they are in the 1° T cell assay. Thus, despite their activity, they still demonstrate preferential activation of the T cell IL-4 receptor.

Example 7
Biological Response of IL-4 Muteins in 1° T cell Assays

FIGS. 4A and B show dose-response curves of the T cell-selective agonist muteins in a representative assay using cells from a normal donor. IL-4 was included as an internal control on each plate used to assay mutein activity; a representative curve is shown. FIG. 6A is the dose-response curve for R121E versus wild-type IL-4. Similarly, FIG. 6B–F are the dose-response curves for R121P, Y124Q, Y124R, Y124A/S125A, and R121T/E122F/Y124Q, respectively, versus wild-type IL-4. Activities have been normalized relative to the IL-4 control responses. Muteins R121E, R121P, and R121T/E122F/Y124Q are more potent than wild-type IL-4, although R121T/E122F/Y124Q is only a partial agonist in this assay. Although not as potent as wild-type IL-4 in this assay, muteins Y124Q, Y124R, and Y124A/S125A are still effective partial agonists ($R_{max}$ values 60–70% of wild-type). In FIG. 6, activity is relative to the IL-4 response seen in the same plate for each mutein. Of particular note are muteins R121E and Y124Q, which show significant activity in the T cell assay yet no apparent activity in the HUVEC assay. Each of these muteins is a clear T cell-selective agonist.

Example 8

Antagonism of HUVEC IL-4-induced IL-6 Secretion by T Cell Selective Muteins

T cell-selective IL-4 muteins R121E (●) and Y124Q (▽), and the IL-4 antagonist R121D/Y124D (○) (FIG. 7), were titrated against a constant concentration of 100 pM IL-4. The IL-4 antagonist R121D/Y124D antagonizes IL-4 with a $K_I$ of ~1.5 nM under these conditions. HUVEC do not express IL-2R γ, but do express the IL-4 receptor γ-like subunit. The substituted residues of R121E and Y124Q are in the D-helix of IL-4 and thus only affect interactions of IL-4 with IL-2Rγ (functional interaction) and the γ-like subunit (no or non-functional interaction), but do not affect the ability of these muteins to bind to IL-4Rα. Thus, the T cell-selective agonists R121E and Y124Q, by virtue of their ability to selectively interact with IL-2Rγ on T cells without promoting activation of the γ-like receptor subunit on endothelial cells, are able to compete IL-4-induced responses on these endothelial cells ($K_I$~0.8–1 nM under these conditions). Such antagonism by T cell-selective IL-4 muteins may antagonize the effects of endogenously produced IL-4 on endothelial cells during T cell-directed therapy with said muteins.

Examples 9

Biological Response of IL-4 Mutein R121D

The IL-4 mutein R121D (Arg-121 substituted with Asp) was generated as described and assayed in the 1° T cell and HUVEC assays. Referring to FIGS. 8A and 8B, data is shown for IL-4 (○) and R121D (●) in both the T cell (FIG. 8A) and the HUVEC (FIG. 8B) assays. In the T cell assay, R121D exhibited an $EC_{50}$ of ~100 pM and an $R_{max}$ value of ~60% relative to wild-type IL-4. It was inactive in the HUVEC assay ($EC_{50}$=●; $R_{max}$=○). These results demonstrate that the single substitution of Arg-121 of human IL-4 with Asp yields a protein that has selective activity on T cells, and lacks any apparent activity on endothelial cells. Although the mutein R121D is a partial agonist in the T cell assay, it is more potent than wild-type IL-4. However, like mutein R121E, R121D exhibits no activity in the HUVEC assay, demonstrating that it is a clear T cell-selective agonist.

Example 10

Biological Activity of IL-4 Mutein T13D/R121E

The IL-4 mutein T13D/R121E (Thr-13 substituted with Asp together with Arg-121 substituted with Glu) was generated as described and assayed in the 1° T cell and HUVEC assays. Specifically with reference to FIGS. 9A–B, in the T cell assay (Panel A), T13D/R121E (▲) exhibited an $EC_{50}$ of 100 pM, about 2–3-fold better than IL-4 (○) or R121E (Δ), and an $R_{max}$ value of 100% relative to IL-4. In HUVEC antagonist assays (Panel B), T13D/R121E (Δ) was ~27-fold more potent an antagonist of IL-4 activity than R121E (Δ), exhibiting an $IC_{50}$ of ~2.2 nM vs. ~60 nM, respectively. The substitution of Thr-13 to Asp increases the potency of the T13D/R121E relative to R121E (both as an agonist in the T cell assay, and as an antagonist in the HUVEC assay), while the substitution Arg-121 to Glu confers T cell-selective activity to T13D/R121E (full agonist in the T cell assay, IL-4 antagonist in the HUVEC assay).

Example 11

Evaluation of the IL-4 Selective Agonist in the Pathology Model

Adult male cynomolgus monkeys (*Macaca fasicularis,* Charles River Primate Imports, Boston, Mass.), weighing approximately 4 to 6 kg are utilized for these studies. Animals are housed individually in environmentally controlled rooms in open mesh cages and provided food twice daily and water ad libitum. Each animal is fasted for approximately 12 hr prior to the first day of study.

For each study animals are anesthetized with an intramuscular injection of ketamine hydrochloride (Ketaset, 10 mg/kg). The upper back area of each animal is sheared and cleaned with a 70% alcohol-betadine solution. IL-4, IL-4 selective agonist or vehicle (0.2% human serum albumin, HSA) is injected intradermally into the backs of animals in a volume of 0.1 ml using a 1 ml tuberculin syringe. The injected sites are separated by at least 10 cm and marked with an indelible marker. Tissue biopsy samples are obtained using a 6 mm punch biopsy tool and samples are placed in OCT and snap frozen in liquid nitrogen. Biopsies are obtained at 0, 4, 8 and 24 hrs post injection.

The systemic response to IL-4, IL-4 selective agonist or vehicle is assessed in the following manner. Test article is administered subcutaneously twice daily (approximately 10–12 hr apart) over four consecutive days in a volume of 0.1 ml/kg at dosages of 0, 2.5, 25 or 250 ug/kg resulting in a total daily dose of 0, 5, 50 and 500 ug/kg, respectively. A peripheral blood sample is obtained from each animal prior to the first injection of vehicle or IL-4 and at the beginning of each day of the study, and aliquots analyzed for complete blood cell counts and differentials, and flow cytometry analysis of peripheral blood mononuclear cell surface markers. The remainder of the blood sample is centrifuged and plasma aliquots stored at −70° C. for subsequent analysis of chemokine levels.

Frozen sections are prepared and allowed to equilibrate to room temperature, air dried and fixed in acetone at 4 C. for 5 minutes. Slides are transferred to 10 mM PBS with 0.1% BSA for 5 minutes. VCAM-1 is localized with the use of C313.3, a monoclonal antibody to human VCAM-1. An irrelevant, isotype-matched immunoglobulin at the appropriate concentration is used as a negative control. Endogenous biotin is blocked using the Vector Biotin blocking kit (Vector Laboratories, Burlingame, Calif.). Sections are incubated 1.5 hr at room temperature in a humid chamber with the indicated antisera diluted in PBS with 0.1% BSA and 1% normal rabbit serum. After three washes with PBS, the slides are stained with the Vector ABC Elite kit according to manufacturers directions and the antibody conjugate detected by incubating the slides in 3-amino-9-ethylcarbazole/hydrogen peroxide (AEC substrate kit, Vector). Sections are washed thoroughly in 0.1 M acetate buffer, washed in distilled water and mounted in Lerner AQUA-MOUNT (Lerner Laboratories, Pittsburgh, Pa.).

Specimens are scored by two independent observers in a blinded manner using set scales between 0 and 3+, designed to assess the intensity as well as distribution of staining. The scoring system for VCAM-1 expression is: 0 absent or faint staining of occasional vessel; 1+faint staining of several vessels; 2+moderate intensity staining of most vessels; 3+ intense staining of most vessels. Blood vessels are identified in serial sections stained for von Willebrands Factor (polyclonal rabbit anti-human VWF; Dakoplatts, Carpinteria, Calif.).

Analysis of erythrocyte count, hematocrit, leukocyte count and platelet counts are performed on heparinized blood samples with a Serono 9000 Blood Analyzer (Baker Diagnostics, Allentown, Pa.). Leukocyte differentials are evaluated on Diff-Quick stained blood smears where a total of two hundred cells are counted and the percentage of each cell type was recorded.

Analysis of peripheral blood mononuclear cell (PBMC) surface markers is performed in the following manner. A 4 ml sample of heparinized blood is diluted in Hanks Balanced Salt Solution (HBSS, without Mg++ or Ca++) and layered onto 4 ml of Percoll (1.070 gm/ml density). The tubes are centrifuged at 1800 rpm (Beckman GS-6R) for 20 minutes at 24 C. The lymphocyte containing layer is aspirated and centrifuged at 1100 rpm for 10 minutes. The resultant cell pellet is resuspended in 6 ml of phosphate buffered saline (PBS) containing 0.1% Azide and 5% goat serum. Aliquots of 1 ml are utilized for cell surface marker analysis as described below.

Antibodies against CD2, CD4, CD8, CD11b, CD16, CD25, CD49 and HLA-DR (R&D Systems, Minneapolis, Minn.) are utilized for analysis by flow cytometry. Twenty ul aliquots of marker antibodies are incubated with 1 ml aliquots of cell suspension in the dark for 60 minutes at 4 C., and samples centrifuged (1000 rpm, 10 min at 4 C.). The pellets are washed three times with 1 ml of PBS containing 0.1% azide and 5% goat serum, followed by FACs analysis.

Plasma samples obtained during each study are analyzed for levels of MCP-1 by specific ELISA. Briefly, 96 well plates (Nunc, Kamstrup, Denmark) are coated with 50 ul/well rabbit anti-MCP-1 for 16 hr at 4 C. and then washed in PBS, pH 7.5, 0.05% Tween-20 (wash buffer). Non specific binding sites are blocked with 2% BSA in PBS (200 ul) and the plates incubated for 90 minutes at 37 C. Plates are rinsed three times with wash buffer, and diluted (neat, 1:5 and 1:10) test sample (50 ul) in duplicate is added, followed by incubation for 1 hr at 37 C. Plates are washed four times, and 50 ul/well biotinylated rabbit anti-MCP-1 is added for 45 minutes at 37 C. Plates are washed four times, streptavidin-peroxidase conjugate (100 ug/ml) (Dakopatts, Carpinteria, Calif.) is added and the plates are incubated for 30 minutes at 37 C. The plates are washed three times, and 100 ul chromogen substrate (0.67 mg/ml orthophenylenediamine dichloride (Dakopatts, Carpinteria, Calif.) is added. The plates are incubated at 25 C. for 6 minutes and the reaction is terminated with 50 ul/well of 3 M $H_2SO_4$ solution in wash buffer plus 2% FCS. Plates are read at 490 nm in an ELISA reader. Standards are 0.5 log dilutions of recombinant MCP-1 from 100 ng/ml to 1 pg/ml (50 ul/well). The ELISA consistently detects MCP-1 concentrations>50 pg/ml.

Example 12

Treatment of Multiple Sclerosis with IL-4 Selective Agonist

The use of an animal model as a predictor for pharmacological utility in humans is a well-accepted research tool. Initial testing of the IL-4 selective agonist for multiple sclerosis (MS) is conducted in a marmoset model using recombinant human IL-4 selective agonist protein. These studies are conducted to examine the effect of prophylactic and therapeutic treatment on disease induction and severity for both the acute symptomology as well as chronic relapsing-remitting disease.

Experimental autoimmune encephalomyelitis (EAE) is a CD4+ T cell-mediated autoimmune, inflammatory disease of the central nervous system. Induction of EAE is induced in marmosets (C. jacchus) weighing 300 to 400 gm by immunization with 200 mg of fresh-frozen postmortem human brain white matter homogenate (BH) emulsified with complete Freund's adjuvant (CFA) containing 3 mg/ml of killed Mycobacterium tuberculosis as described in Massacesi et al., Ann. Neurol., 37:519 (1995). On the day of immunization and again 2 days later, $10^{10}$ inactivated Bordetella pertussis organisms are diluted in 10 ml of saline solution and administered intravenously.

EAE is assessed by clinical and pathological criteria. A standardized scoring system is employed to record the severity of clinical disease: 0=normal neurological findings; 1=lethargy, anorexia, weight loss; 2=ataxia, and either paraparesis/monoparesis, sensory loss, or brainstem syndrome including gaze palsy, or blindness; 3=paraplegia or hemiplegia; 4=quadriplegia.

Magnetic resonance imaging (MRI) has been shown to be a useful technique to characterize early as well as late immune mediated lesions of MS (Stewart et al., Brain, 114:1069 (1991). MRI is used to evaluate animals after immunization to monitor progression of disease over time. MRI data is collected on a Picker International NMR Cryogenic '2000' system, operating at a field strength of 0.15 Tesla; a receiver coil with an aperture of 15 cm to obtain the images. Multislice spin-echo and inversion-recovery pulse sequences are employed. Echo-delays times of either 40 and 60 ms, or 40 and 80 ms are used in the spin-echo sequences. In the inversion-recovery sequences the 180-90 interpulse delay is 400 ms.

Marmosets are anesthetized with ketamine hydrochloride and placed in the scanner using a laser available for patient alignment such that the inner canthi of the eyes are aligned perpendicular to the direction of the static magnetic field. Animals are scanned before immunization and then daily from day 9 after immunization. Prior to scanning each day, animals are checked for signs of neurological impairment.

Animals are sacrificed at different times after immunization. The CNS is removed and fixed in 10% formalin. Paraffin sections of brain and spinal cord are prepared and stained with hematoxylin and eosin. Each coronal brain section or horizontal spinal cord section is analyzed for histopathological findings of inflammation and demyelination according to an arbitrary scale: inflammation; 0=no inflammation present, +=rare perivascular cuffs/average whole section; ++=moderate numbers of perivascular cuffs/section; may have meningeal inflammation; +++= widespread perivascular cuffing and parenchymal infiltration by inflammatory cells. Demyelination score; 0=no demyelination present; +=rare foci of demyelination; ++=moderate demyelination; +++=extensive demyelination with large confluent lesions.

For pretreatment studies on acute disease pathology, test drug is administered subcutaneously at a dosage range between 1 and 500 ug/kg following a dosing regimen of 1 administration per day to 1 administration per week prior to the onset of disease symptoms. For therapeutic intervention in existing disease, test article is administered subcutaneously at a dose range between 1 and 500 ug/kg following an extended dosing regimen of 1 treatment per day to 1 treatment per week over the course of several months.

Example 13
Treatment of Rheumatoid Arthritis

Rheumatoid arthritis (RA) is a debilitating inflammatory disease in which chronic activation of resident and infiltrating synovial cells causes destruction of cartilage and bone and leads to fibrosis and loss of function. Cytokines released from activated T cells are thought to play a role in the maintenance of the chronic inflammatory reaction.

RA is induced in DBA/1 mice using type II collagen as described by Joosten et al., Arthritis & Rheumatism; 39:797 (1996). Collagen induced arthritis (CIA) is induced by immunizing mice via intradermal injection at the base of the tail with 100 ul of emulsion containing 100 ug of collagen. On day 21, animals are given a intraperitoneal booster injection of type II collagen (100 ug) dissolved in phosphate buffered saline (PBS).

Assessment of CIA is performed by examining the mice visually for the appearance of arthritis in the peripheral joints and scores for arthritis severity are assigned. Mice are considered to have arthritis when significant changes in redness and/or swelling is noted in the digits or in other parts of a minimum of 2 paws.

Clinical severity of arthritis is scored on a scale of 0–2 for each paw according to changes in redness and swelling (0=no change, 0.5=significant, 1.0=moderate, 1.5=marked and 2.0=severe maximal swelling and redness. Scoring is assessed by at least two blinded observers.

At the end of the study, some of the animals are sacrificed and paw and joint tissue is obtained for pathological and histopathology examination. The tissue is processed for immunohistochemical staining (frozen sections) or fixed and embedded in paraffin, sectioned and stained with H&E for analysis of cellular infiltration.

Evaluation of a murine analog of the IL-4 selective agonist of the present invention in the CIA model is performed with the use of a murine equivalent protein molecule. One of ordinary skill in the art is capable of comparing the murine IL-4 structure with the human IL-4 structure, generating parallel murine IL-4 muteins, and making any necessary adjustments based on responses in in vitro assays utilizing cell lines expressing either IL-4Rα/IL-2Rγ or IL-4Rα/γ-like subunit in a manner analogous to that used for human IL-4 muteins with T cells and HUVEC. Animals are dosed one day prior to the booster administration of collagen and kept on a dosing regimen ranging between once a day to once a week for the duration of the study (40+ days). Animals are dosed with a range of concentrations of IL-4 selective agonist ranging between 1 to 100 ug/kg.

Example 14
Treatment of Insulin Dependent Diabetes Mellitus (IDDM)

There is some evidence in the literature of Th1 cell involvement in IDDM in humans and animal models of human disease. Nonobese diabetic (NOD) mice are utilized to examine the efficacy of a murine IL-4 equivalent of IL-4 selective agonist in treating IDDM. One of ordinary skill in the art is capable of comparing the murine IL-4 structure with the human IL-4 structure, generating parallel murine IL-4 muteins, and making any necessary adjustments based on responses in in vitro assays utilizing cell lines expressing either IL-4Rα/IL-2Rγ or IL-4Rα/γ-like subunit in a manner analogous to that used for human IL-4 muteins with T cells and HUVEC. Prediabetic NOD mice (approximately 7 wks) exhibit a proliferative unresponsiveness in vitro after T cell stimulation. The timing of this unresponsiveness is not related to insulitis and persists until the onset of diabetes which occurs at 24 wks of age.

Evaluation of the IL-4 selective agonist in NOD mice is conducted similar to studies reported by Rapoport et al., J. Exp Med; 178; p. 87 (1993). NOD mice are injected with test material at approximately 3 wks of age following a dosing regimen of once daily treatment or once a week treatment over the course of 12 weeks until the mice are 15 wks old. A control group of animals will receive treatment with a inert protein equivalent.

Mice will we tested for glycosuria using Tes-Tape and diagnosed for diabetes as determined by being glycosuria for at least two consecutive weeks. At the end of 52 wks, animals are sacrificed to obtain various organs and tissue for pathology evaluation. Tissue from the pancreas, submandibular salivary glands and kidney from each mouse is fixed and embedded in paraffin, sectioned and stained. Aldehyde fuchsin staining of pancreas sections is used to examine the extent to which insulitic infiltrates have reduced the mass of granulated β cells. Splenic leukocytes are counted by FAC-Scan analyses using anti-Thy-1.2, anti-CD4 and anti-CD8 mabs in ascites as described by Zipris et al., J. Immunol 146; p. 3763 (1991).

Other embodiments of the invention will become apparent to one of skill in the art. This invention teaches how to obtain muteins not specifically described herein but which have T cell activating ability and reduced endothelial cell activating ability, and thereby those muteins come within the spirit and scope of the invention. The concept and experimental approach described herein should be applicable to other cytokines utilizing heterologous multimeric receptor systems, in particular IL-2 and related cytokines (e.g., IL-7, IL-9 and IL- 15), IL-10, interferon α, and interferon γ.

SEQUENCES

The following sequences are contained within this application:
SEQ ID NO: 1: hIL-4 (amino acid)
SEQ ID NO: 2: hIL-4 (amino acid, cDNA)
SEQ ID NO: 3: R121A (amino acid, cDNA)
SEQ ID NO: 4: R121D (amino acid, cDNA)
SEQ ID NO: 5: R121E (amino acid, cDNA)
SEQ ID NO: 6: R121F (amino acid, cDNA)
SEQ ID NO: 7: R121H (amino acid, cDNA)
SEQ ID NO: 8: R121I (amino acid, cDNA)
SEQ ID NO: 9: R121K (amino acid, cDNA)
SEQ ID NO: 10: R121N (amino acid, DNA)
SEQ ID NO: 11: R121P (amino acid, cDNA)
SEQ ID NO: 12: R121T (amino acid, cDNA)
SEQ ID NO: 13: R121W (amino acid, cDNA)
SEQ ID NO: 14: Y124A (amino acid, cDNA)

SEQ ID NO: 15: Y124Q (amino acid, cDNA)
SEQ ID NO: 16: Y124R (amino acid, cDNA)
SEQ ID NO: 17: Y212S (amino acid, cDNA)
SEQ ID NO: 18: R121T (amino acid, cDNA)
SEQ ID NO: 19: Y124A/S125A (amino acid, cDNA)
SEQ ID NO: 20: T13D/R121E (amino acid, cDNA)
SEQ ID NO: 21: R121T/E122F/Y124Q (amino acid, cDNA)
SEQ ID NO: 22: 5' PCR Primer, IL-4
SEQ ID NO: 23: 3' PCR Primer, IL-4
SEQ ID NO: 24: Mutagenesis Primer for R121A
SEQ ID NO: 25: Mutagenesis Primer for R121D
SEQ ID NO: 26: Mutagenesis Primer for R121E
SEQ ID NO: 27: Mutagenesis Primer for R121F
SEQ ID NO: 28: Mutagenesis Primer for R122H
SEQ ID NO: 29: Mutagenesis Primer for R121I
SEQ ID NO: 30: Mutagenesis Primer for R121K
SEQ ID NO: 31: Mutagenesis Primer for R121N
SEQ ID NO: 32: Mutagenesis Primer for R121P
SEQ ID NO: 33: Mutagenesis Primer for R121T
SEQ ID NO: 34: Mutagenesis Primer for R121W
SEQ ID NO: 35: Mutagenesis Primer for Y124A
SEQ ID NO: 36: Mutagenesis Primer for Y124Q
SEQ ID NO: 37: Mutagenesis Primer for Y124R
SEQ ID NO: 38: Mutagenesis Primer for Y124S
SEQ ID NO: 39: Mutagenesis Primer for Y124T
SEQ ID NO: 40: Mutagenesis Primer for Y124A/S125A
SEQ ID NO: 41: Mutagenesis Primer for T13D
SEQ ID NO: 42: Mutagenesis Primer for R121T/E122F/Y124Q Note: for the T13D/R121E mutein, the primers SEQ ID NOs: 26 and 41 are used.

We claim:

1. A polynucleotide molecule encoding a human IL-4 mutein wherein surface exposed residues of the D helix are mutated whereby the resulting mutein causes T-cell proliferation, and causes reduced IL-6 secretion from HUVEC's, relative to wild type IL-4.

2. The polynucleotide molecule of claim 1 wherein the mutation is at position 121 relative to wild type IL-4.

3. The polynucleotide molecule of claim 2 wherein the mutation is R121A.

4. The polynucleotide molecule of claim 2 wherein the mutation is R121D.

5. The polynucleotide molecule of claim 2 wherein the mutation is R121E.

6. The polynucleotide molecule of claim 2 wherein the mutation is R121F.

7. The polynucleotide molecule of claim 2 wherein the mutation is R121H.

8. The polynucleotide molecule of claim 2 wherein the mutation is R121I.

9. The polynucleotide molecule of claim 2 wherein the mutation is R121K.

10. The polynucleotide molecule of claim 2 wherein the mutation is R121N.

11. The polynucleotide molecule of claim 2 wherein the mutation is R121P.

12. The polynucleotide molecule of claim 2 wherein the mutation is R121T.

13. The polynucleotide molecule of claim 2 wherein the mutation is R121W.

14. The polynucleotide molecule of claim 1 wherein the mutation is at position 122 relative to wild type IL-4.

15. The polynucleotide molecule of claim 14 wherein the mutation is E122F.

16. The polynucleotide molecule of claim 1 wherein the mutation is at position 124 relative to wild type IL-4.

17. The polynucleotide molecule of claim 16 wherein the mutation is Y124A.

18. The polynucleotide molecule of claim 16 wherein the mutation is Y124Q.

19. The polynucleotide molecule of claim 16 wherein the mutation is Y124R.

20. The polynucleotide molecule of claim 16 wherein the mutation is Y124S.

21. The polynucleotide molecule of claim 16 wherein the mutation is Y124T.

22. The polynucleotide molecule of claim 1 wherein mutations are at positions 124 and 125 relative to wild type IL-4.

23. The polynucleotide molecule of claim 22 wherein the mutations are Y124A and S125A.

24. The polynucleotide molecule of claim 1 wherein mutations are at positions 121, 122, and 124 relative to wild type IL-4.

25. The polynucleotide molecule of claim 24 wherein the mutations are R121T, E122F, and Y124Q.

* * * * *

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
        (A) LENGTH: 129
        (B) TYPE: amino acid
        (C) STRANDEDNESS: single
        (D) TOPOLOGY: linear (ii) MOLECULE TYPE: protein
        (A) DESCRIPTION: human Interleukin-4 protein (iii) HYPOTHETICAL: no (iv) ANTI-SENSE: no (xi) SEQUENCE DESCRIPTION: SEQ ID NO: 1:

His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr
20                  25                  30

Asp Ile Phe Ala Ala Ser Lys Asn Thr Thr Glu Lys Glu Thr Phe
35                  40                  45

Cys Arg Ala Ala Thr Val Leu Arg Gln Phe Tyr Ser His His Glu
50                  55                  60

Lys Asp Thr Arg Cys Leu Gly Ala Thr Ala Gln Gln Phe His Arg
65                  70                  75

His Lys Gln Leu Ile Arg Phe Leu Lys Arg Leu Asp Arg Asn Leu
80                  85                  90

Trp Gly Leu Ala Gly Leu Asn Ser Cys Pro Val Lys Glu Ala Asn
95                  100                 105

Gln Ser Thr Leu Glu Asn Phe Leu Glu Arg Leu Lys Thr Ile Met
110                 115                 120

Arg Glu Lys Tyr Ser Lys Cys Ser Ser
125

(2) INFORMATION FOR SEQ ID NO: 2:

(i) SEQUENCE CHARACTERISTICS:
        (A) LENGTH: 462
        (B) TYPE: nucleic acid -continued (C) STRANDEDNESS: single
(D) TOPOLOGY: linear (ii) MOLECULE TYPE: cDNA
(A) DESCRIPTION: human IL-4 protein (iii) HYPOTHETICAL: no (iv) ANTI-SENSE: no (xi) SEQUENCE DESCRIPTION: SEQ ID NO: 2:

| ATG GGT CTC ACC TCC GAA CTG CTT CCC CCT CTG TTC TTC CTG CTA | 45 |
| Met Gly Leu Thr Ser Gln Leu Leu Pro Pro Leu Phe Phe Leu Leu | |
| 1           5                   10                  15      | |

| GCA TGT GCC GGC AAC TTT GTC CAC GGA CAC AAG TGC GAT ATC ACC | 90 |
| Ala Cys Ala Gly Asn Phe Val His Gly His Lys Cys Asp Ile Thr | |
| 20              25                  30                      | |

| TTA CAG GAG ATC ATC AAA ACT TTG AAC AGC CTC ACA GAG CAG AAG | 135 |
| Leu Gln Glu Ile Ile Lys Thr Leu Asn Ser Leu Thr Glu Gln Lys | |
| 35              40                  45                      | |

| ACT CTG TGC ACC GAG TTG ACC GTA ACA GAC ATC TTT GCT GCC TCC | 180 |
| Thr Leu Cys Thr Glu Leu Thr Val Thr Asp Ile Phe Ala Ala Ser | |
| 50              55                  60                      | |

| AAG AAC ACA ACT GAG AAG GAA ACC TTC TGC AGG GCT GCG ACT GTG | 225 |
| Lys Asn Thr Thr Glu Lys Glu Thr Phe Cys Arg Ala Ala Thr Val | |
| 65              70                  75                      | |

| CTC CGG CAG TTC TAC AGC CAC CAT GAG AAG GAC ACT CGC TGC CTG | 270 |
| Leu Arg Gln Phe Tyr Ser His His Glu Lys Asp Thr Arg Cys Leu | |
| 80              85                  90                      | |

| GGT GCG ACT GCA CAG CAG TTC CAC AGG CAC AAG CAG CTG ATC CGA | 315 |
| Gly Ala Thr Ala Gln Gln Phe His Arg His Lys Gln Leu Ile Arg | |
| 95              100                 105                     | |

| TTC CTG AAA CGG CTC GAC AGG AAC CTC TGG GGC CTG GCG GGC TTG | 360 |
| Phe Leu Lys Arg Leu Asp Arg Asn Leu Trp Gly Leu Ala Gly Leu | |
| 110             115                 120                     | |

| AAT TCC TGT CCT GTG AAG GAA GCC AAC CAG AGT ACG TTG GAA AAC | 405 |
| Asn Ser Cys Pro Val Lys Glu Ala Asn Gln Ser Thr Leu Glu Asn | |
| 125             130                 135                     | |

| TTC TTG GAA AGG CTA AAG ACG ATC ATG AGA GAG AAA TAT TCA AAG | 450 |
| Phe Leu Glu Arg Leu Lys Thr Ile Met Arg Glu Lys Tyr Ser Lys | |
| 140             145                 150                     | |

| TGT TCG AGC TAG | 462 |
| Cys Ser Ser End | |
| 153 | |

(2) INFORMATION FOR SEQ ID NO: 3:

(i) SEQUENCE CHARACTERISTICS:
(A) LENGTH: 462
(B) TYPE: nucleic acid
(C) STRANDEDNESS: single
(D) TOPOLOGY: linear (ii) MOLECULE TYPE: cDNA
(A) DESCRIPTION: hIL-4/R121A (iii) HYPOTHETICAL: no (iv) ANTI-SENSE: no (xi) SEQUENCE DESCRIPTION: SEQ ID NO: 3:

| ATG GGT CTC ACC TCC GAA CTG CTT CCC CCT CTG TTC TTC CTG CTA | 45 |
| Met Gly Leu Thr Ser Gln Leu Leu Pro Pro Leu Phe Phe Leu Leu | |
| 1           5                   10                  15      | |

| GCA TGT GCC GGC AAC TTT GTC CAC GGA CAC AAG TGC GAT ATC ACC | 90 |

```
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125                 130                 135

TTC TTG GAA AGG CTA AAG ACG ATC ATG GCT GAG AAA TAT TCA AAG        450
Phe Leu Glu Arg Leu Lys Thr Ile Met Ala Glu Lys Tyr Ser Lys
140                 145                 150

TGT TCG AGC TAG                                                     462
Cys Ser Ser End
153

(2) INFORMATION FOR SEQ ID NO: 4:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121D (iii) HYPOTHETICAL: no (iv) ANTI-SENSE: no (xi) SEQUENCE DESCRIPTION: SEQ ID NO: 4:

ATG GGT CTC ACC TCC GAA CTG CTT CCC CCT CTG TTC TTC CTG CTA         45
Met Gly Leu Thr Ser Gln Leu Leu Pro Pro Leu Phe Phe Leu Leu
1                   5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
```

-continued

```
            80                     85                     90
GGT GCG ACT GCA CAG CAG TTC CAC AGG CAC AAG CAG CTG ATC CGA         315
Gly Ala Thr Ala Gln Gln Phe His Arg His Lys Gln Leu Ile Arg
 95                    100                    105

TTC CTG AAA CGG CTC GAC AGG AAC CTC TGG GGC CTG GCG GGC TTG         360
Phe Leu Lys Arg Leu Asp Arg Asn Leu Trp Gly Leu Ala Gly Leu
110                    115                    120

AAT TCC TGT CCT GTG AAG GAA GCC AAC CAG AGT ACG TTG GAA AAC         405
Asn Ser Cys Pro Val Lys Glu Ala Asn Gln Ser Thr Leu Glu Asn
125                    130                    135

TTC TTG GAA AGG CTA AAG ACG ATC ATG GAC GAG AAA TAT TCA AAG         450
Phe Leu Glu Arg Leu Lys Thr Ile Met Asp Glu Lys Tyr Ser Lys
140                    145                    150

TGT TCG AGC TAG                                                      462
Cys Ser Ser End
153

(2) INFORMATION FOR SEQ ID NO: 5:

(i) SEQUENCE CHARACTERISTICS:
           (A) LENGTH: 462
           (B) TYPE: nucleic acid
           (C) STRANDEDNESS: single
           (D) TOPOLOGY: linear (ii) MOLECULE TYPE: cDNA
           (A) DESCRIPTION: hIL-4/R121E (iii) HYPOTHETICAL: no (iv) ANTI-SENSE: no (xi) SEQUENCE DESCRIPTION: SEQ ID NO: 5:

ATG GGT CTC ACC TCC CAA CTG CTT CCC CCT CTG TTC TTC CTG CTA          45
Met Gly Leu Thr Ser Gln Leu Leu Pro Pro Leu Phe Phe Leu Leu
 1                      5                     10                     15

GCA TGT GCC GGC AAC TTT GTC CAC GGA CAC AAG TGC GAT ATC ACC          90
Ala Cys Ala Gly Asn Phe Val His Gly His Lys Cys Asp Ile Thr
20                     25                     30

TTA CAG GAG ATC ATC AAA ACT TTG AAC AGC CTC ACA GAG CAG AAG         135
Leu Gln Glu Ile Ile Lys Thr Leu Asn Ser Leu Thr Glu Gln Lys
35                     40                     45

ACT CTG TGC ACC GAG TTG ACC GTA ACA GAC ATC TTT GCT GCC TCC         180
Thr Leu Cys Thr Glu Leu Thr Val Thr Asp Ile Phe Ala Ala Ser
50                     55                     60

AAG AAC ACA ACT GAG AAG GAA ACC TTC TGC AGG GCT GCG ACT GTG         225
Lys Asn Thr Thr Glu Lys Glu Thr Phe Cys Arg Ala Ala Thr Val
65                     70                     75

CTC CGG CAG TTC TAC AGC CAC CAT GAG AAG GAC ACT CGC TGC CTG         270
Leu Arg Gln Phe Tyr Ser His His Glu Lys Asp Thr Arg Cys Leu
80                     85                     90

GGT GCG ACT GCA CAG CAG TTC CAC AGG CAC AAG CAG CTG ATC CGA         315
Gly Ala Thr Ala Gln Gln Phe His Arg His Lys Gln Leu Ile Arg
95                     100                    105

TTC CTG AAA CGG CTC GAC AGG AAC CTC TGG GGC CTG GCG GGC TTG         360
Phe Leu Lys Arg Leu Asp Arg Asn Leu Trp Gly Leu Ala Gly Leu
110                    115                    120

AAT TCC TGT CCT GTG AAG GAA GCC AAC CAG AGT ACG TTG GAA AAC         405
Asn Ser Cys Pro Val Lys Glu Ala Asn Gln Ser Thr Leu Glu Asn
125                    130                    135

TTC TTG GAA AGG CTA AAG ACG ATC ATG GAA GAG AAA TAT TCA AAG         450
Phe Leu Glu Arg Leu Lys Thr Ile Met Glu Glu Lys Tyr Ser Lys
140                    145                    150
```

```
TGT TCG AGC TAG                                                          462
Cys Ser Ser End
153

(2) INFORMATION FOR SEQ ID NO: 6:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121F (iii) HYPOTHETICAL: no (iv) ANTI-SENSE: no (xi) SEQUENCE DESCRIPTION: SEQ ID NO: 6:

ATG GGT CTC ACC TCC GAA CTG CTT CCC CCT CTG TTC TTC CTG CTA              45
Met Gly Leu Thr Ser Glu Leu Leu Pro Pro Leu Phe Phe Leu Leu
1               5                   10                  15

GCA TGT GCC GGC AAC TTT GTC CAC GGA CAC AAG TGC GAT ATC ACC              90
Ala Cys Ala Gly Asn Phe Val His Gly His Lys Cys Asp Ile Thr
20              25                  30

TTA CAG GAG ATC ATC AAA ACT TTG AAC AGC CTC ACA GAG CAG AAG             135
Leu Gln Glu Ile Ile Lys Thr Leu Asn Ser Leu Thr Glu Gln Lys
35              40                  45

ACT CTG TGC ACC GAG TTG ACC GTA ACA GAC ATC TTT GCT GCC TCC             180
Thr Leu Cys Thr Glu Leu Thr Val Thr Asp Ile Phe Ala Ala Ser
50              55                  60

AAG AAC ACA ACT GAG AAG GAA ACC TTC TGC AGG GCT GCG ACT GTG             225
Lys Asn Thr Thr Glu Lys Glu Thr Phe Cys Arg Ala Ala Thr Val
65              70                  75

CTC CGG CAG TTC TAC AGC CAC CAT GAG AAG GAC ACT CGC TGC CTG             270
Leu Arg Gln Phe Tyr Ser His His Glu Lys Asp Thr Arg Cys Leu
80              85                  90

GGT GCG ACT GCA CAG CAG TTC CAC AGG CAC AAG CAG CTG ATC CGA             315
Gly Ala Thr Ala Gln Gln Phe His Arg His Lys Gln Leu Ile Arg
95              100                 105

TTC CTG AAA CGG CTC GAC AGG AAC CTC TGG GGC CTG GCG GGC TTG             360
Phe Leu Lys Arg Leu Asp Arg Asn Leu Trp Gly Leu Ala Gly Leu
110             115                 120

AAT TCC TGT CCT GTG AAG GAA GCC AAC CAG AGT ACG TTG GAA AAC             405
Asn Ser Cys Pro Val Lys Glu Ala Asn Gln Ser Thr Leu Glu Asn
125             130                 135

TTC TTG GAA AGG CTA AAG ACG ATC ATG TTT GAG AAA TAT TCA AAG             450
Phe Leu Glu Arg Leu Lys Thr Ile Met Phe Glu Lys Tyr Ser Lys
140             145                 150

TGT TCG AGC TAG                                                         462
Cys Ser Ser End
153

(2) INFORMATION FOR SEQ ID NO: 7:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121H
```

-continued (iii) HYPOTHETICAL: no (iv) ANTI-SENSE: no (xi) SEQUENCE DESCRIPTION: SEQ ID NO: 7:

```
ATG GGT CTC ACC TCC GAA CTG CTT CCC CCT CTG TTC TTC CTG CTA        45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC        90
Ala Cys Ala Gly Asn Phe Val His Gly His Lys Cys Asp Ile Thr
20              25                  30

TTA CAG GAG ATC ATC AAA ACT TTG AAC AGC CTC ACA GAG CAG AAG       135
Leu Gln Glu Ile Ile Lys Thr Leu Asn Ser Leu Thr Glu Gln Lys
35              40                  45

ACT CTG TGC ACC GAG TTG ACC GTA ACA GAC ATC TTT GCT GCC TCC       180
Thr Leu Cys Thr Glu Leu Thr Val Thr Asp Ile Phe Ala Ala Ser
50              55                  60

AAG AAC ACA ACT GAG AAG GAA ACC TTC TGC AGG GCT GCG ACT GTG       225
Lys Asn Thr Thr Glu Lys Glu Thr Phe Cys Arg Ala Ala Thr Val
65              70                  75

CTC CGG CAG TTC TAC AGC CAC CAT GAG AAG GAC ACT CGC TGC CTG       270
Leu Arg Gln Phe Tyr Ser His His Glu Lys Asp Thr Arg Cys Leu
80              85                  90

GGT GCG ACT GCA CAG CAG TTC CAC AGG CAC AAG CAG CTG ATC CGA       315
Gly Ala Thr Ala Gln Gln Phe His Arg His Lys Gln Leu Ile Arg
95              100                 105

TTC CTG AAA CGG CTC GAC AGG AAC CTC TGG GGC CTG GCG GGC TTG       360
Phe Leu Lys Arg Leu Asp Arg Asn Leu Trp Gly Leu Ala Gly Leu
110             115                 120

AAT TCC TGT CCT GTG AAG GAA GCC AAC CAG AGT ACG TTG GAA AAC       405
Asn Ser Cys Pro Val Lys Glu Ala Asn Gln Ser Thr Leu Glu Asn
125             130                 135

TTC TTG GAA AGG CTA AAG ACG ATC ATG CAC GAG AAA TAT TCA AAG       450
Phe Leu Glu Arg Leu Lys Thr Ile Met His Glu Lys Tyr Ser Lys
140             145                 150

TGT TCG AGC TAG                                                    462
Cys Ser Ser End
153
```

(2) INFORMATION FOR SEQ ID NO: 8:

(i) SEQUENCE CHARACTERISTICS:
(A) LENGTH: 462
(B) TYPE: nucleic acid
(C) STRANDEDNESS: single
(D) TOPOLOGY: linear (ii) MOLECULE TYPE: cDNA
(A) DESCRIPTION: hIL-4/R121I (iii) HYPOTHETICAL: no (iv) ANTI-SENSE: no (xi) SEQUENCE DESCRIPTION: SEQ ID NO: 8:

```
ATG GGT CTC ACC TCC GAA CTG CTT CCC CCT CTG TTC TTC CTG CTA        45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC        90
Ala Cys Ala Gly Asn Phe Val His Gly His Lys Cys Asp Ile Thr
20              25                  30

TTA CAG GAG ATC ATC AAA ACT TTG AAC AGC CTC ACA GAG CAG AAG       135
Leu Gln Glu Ile Ile Lys Thr Leu Asn Ser Leu Thr Glu Gln Lys
35              40                  45
```

```
ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125                 130                 135

TTC TTG GAA AGG CTA AAG ACG ATC ATG ATA GAG AAA TAT TCA AAG        450
Phe Leu Glu Arg Leu Lys Thr Ile Met Ile Glu Lys Tyr Ser Lys
140                 145                 150

TGT TCG AGC TAG                                                    462
Cys Ser Ser End
153

(2) INFORMATION FOR SEQ ID NO: 9:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121K (iii) HYPOTHETICAL: no (iv) ANTI-SENSE: no (xi) SEQUENCE DESCRIPTION: SEQ ID NO: 9:

ATG GGT CTC ACC TCC GAA CTG CTT CCC CCT CTG TTC TTC CTG CTA         45
Met Gly Leu Thr Ser Glu Leu Leu Pro Pro Leu Phe Phe Leu Leu
1                   5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95                  100                 105
```

```
TTC CTG AAA CGG CTC GAC AGG AAC CTC TGG GGC CTG GCG GGC TTG         360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC         405
Asn Ser Cys Pro Val Lys Glu Ala Asn Gln Ser Thr Leu Glu Asn
125                 130                 135

TTC TTG GAA AGG CTA AAG ACG ATC ATG AAA GAG AAA TAT TCA AAG         450
Phe Leu Glu Arg Leu Lys Thr Ile Met Lys Glu Lys Tyr Ser Lys
140                 145                 150

TGT TCG AGC TAG                                                     462
Cys Ser Ser End
153

(2) INFORMATION FOR SEQ ID NO: 10:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
         (A) DESCRIPTION: hIL-4/R121N (iii) HYPOTHETICAL: no (iv) ANTI-SENSE: no (xi) SEQUENCE DESCRIPTION: SEQ ID NO: 10:

ATG GGT CTC ACC TCC GAA CTG CTT CCC CCT CTG TTC TTC CTG CTA          45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC          90
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG         135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC         180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG         225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG         270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA         315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG         360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC         405
Asn Ser Cys Pro Val Lys Glu Ala Asn Gln Ser Thr Leu Glu Asn
125                 130                 135

TTC TTG GAA AGG CTA AAG ACG ATC ATG AAC GAG AAA TAT TCA AAG         450
Phe Leu Glu Arg Leu Lys Thr Ile Met Asn Glu Lys Tyr Ser Lys
140                 145                 150

TGT TCG AGC TAG                                                     462
Cys Ser Ser End
153
```

(2) INFORMATION FOR SEQ ID NO: 11:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121P (iii) HYPOTHETICAL: no (iv) ANTI-SENSE: no (xi) SEQUENCE DESCRIPTION: SEQ ID NO: 11:

```
ATG GGT CTC ACC TCC CAA CTG CTT CCC CCT CTG TTC TTC CTG CTA       45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC       90
Ala Cys Ala Gly Asn Phe Val His Gly His Lys Cys Asp Ile Thr
            20                  25                  30

TTA CAG GAG ATC ATC AAA ACT TTG AAC AGC CTC ACA GAG CAG AAG      135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC      180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG      225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG      270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA      315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG      360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC      405
Asn Ser Cys Pro Val Lys Glu Ala Asn Gln Ser Thr Leu Glu Asn
125                 130                 135

TTC TTG GAA AGG CTA AAG ACG ATC ATG CCA GAG AAA TAT TCA AAG      450
Phe Leu Glu Arg Leu Lys Thr Ile Met Pro Glu Lys Tyr Ser Lys
140                 145                 150

TGT TCG AGC TAG                                                  462
Cys Ser Ser End
153
```

(2) INFORMATION FOR SEQ ID NO: 12:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121T (iii) HYPOTHETICAL: no (iv) ANTI-SENSE: no (xi) SEQUENCE DESCRIPTION: SEQ ID NO: 12:

| | |
|---|---|
| ATG GGT CTC ACC TCC GAA CTG CTT CCC CCT CTG TTC TTC CTG CTA<br>Met Gly Leu Thr Ser Gln Leu Leu Pro Pro Leu Phe Phe Leu Leu<br>1               5                   10                  15 | 45 |
| GCA TGT GCC GGC AAC TTT GTC CAC GGA CAC AAG TGC GAT ATC ACC<br>Ala Cys Ala Gly Asn Phe Val His Gly His Lys Cys Asp Ile Thr<br>20              25                  30 | 90 |
| TTA CAG GAG ATC ATC AAA ACT TTG AAC AGC CTC ACA GAG CAG AAG<br>Leu Gln Glu Ile Ile Lys Thr Leu Asn Ser Leu Thr Glu Gln Lys<br>35              40                  45 | 135 |
| ACT CTG TGC ACC GAG TTG ACC GTA ACA GAC ATC TTT GCT GCC TCC<br>Thr Leu Cys Thr Glu Leu Thr Val Thr Asp Ile Phe Ala Ala Ser<br>50              55                  60 | 180 |
| AAG AAC ACA ACT GAG AAG GAA ACC TTC TGC AGG GCT GCG ACT GTG<br>Lys Asn Thr Thr Glu Lys Glu Thr Phe Cys Arg Ala Ala Thr Val<br>65              70                  75 | 225 |
| CTC CGG CAG TTC TAC AGC CAC CAT GAG AAG GAC ACT CGC TGC CTG<br>Leu Arg Gln Phe Tyr Ser His His Glu Lys Asp Thr Arg Cys Leu<br>80              85                  90 | 270 |
| GGT GCG ACT GCA CAG CAG TTC CAC AGG CAC AAG CAG CTG ATC CGA<br>Gly Ala Thr Ala Gln Gln Phe His Arg His Lys Gln Leu Ile Arg<br>95              100                 105 | 315 |
| TTC CTG AAA CGG CTC GAC AGG AAC CTC TGG GGC CTG GCG GGC TTG<br>Phe Leu Lys Arg Leu Asp Arg Asn Leu Trp Gly Leu Ala Gly Leu<br>110             115                 120 | 360 |
| AAT TCC TGT CCT GTG AAG GAA GCC AAC CAG AGT ACG TTG GAA AAC<br>Asn Ser Cys Pro Val Lys Glu Ala Asn Gln Ser Thr Leu Glu Asn<br>125             130                 135 | 405 |
| TTC TTG GAA AGG CTA AAG ACG ATC ATG ACT GAG AAA TAT TCA AAG<br>Phe Leu Glu Arg Leu Lys Thr Ile Met Thr Glu Lys Tyr Ser Lys<br>140             145                 150 | 450 |
| TGT TCG AGC TAG<br>Cys Ser Ser End<br>153 | 462 |

(2) INFORMATION FOR SEQ ID NO: 13:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/R121W (iii) HYPOTHETICAL: no (iv) ANTI-SENSE: no (xi) SEQUENCE DESCRIPTION: SEQ ID NO: 13:

| | |
|---|---|
| ATG GGT CTC ACC TCC GAA CTG CTT CCC CCT CTG TTC TTC CTG CTA<br>Met Gly Leu Thr Ser Gln Leu Leu Pro Pro Leu Phe Phe Leu Leu<br>1               5                   10                  15 | 45 |
| GCA TGT GCC GGC AAC TTT GTC CAC GGA CAC AAG TGC GAT ATC ACC<br>Ala Cys Ala Gly Asn Phe Val His Gly His Lys Cys Asp Ile Thr<br>20              25                  30 | 90 |
| TTA CAG GAG ATC ATC AAA ACT TTG AAC AGC CTC ACA GAG CAG AAG<br>Leu Gln Glu Ile Ile Lys Thr Leu Asn Ser Leu Thr Glu Gln Lys<br>35              40                  45 | 135 |
| ACT CTG TGC ACC GAG TTG ACC GTA ACA GAC ATC TTT GCT GCC TCC<br>Thr Leu Cys Thr Glu Leu Thr Val Thr Asp Ile Phe Ala Ala Ser<br>50              55                  60 | 180 |
| AAG AAC ACA ACT GAG AAG GAA ACC TTC TGC AGG GCT GCG ACT GTG | 225 |

```
Lys Asn Thr Thr Glu Lys Glu Thr Phe Cys Arg Ala Ala Thr Val
 65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
 80                  85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
 95                 100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125                 130                 135

TTC TTG GAA AGG CTA AAG ACG ATC ATG TGG GAG AAA TAT TCA AAG        450
Phe Leu Glu Arg Leu Lys Thr Ile Met Trp Glu Lys Tyr Ser Lys
140                 145                 150

TGT TCG AGC TAG                                                    462
Cys Ser Ser End
153

(2) INFORMATION FOR SEQ ID NO: 14:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: hIL-4/Y124A (iii) HYPOTHETICAL: no (iv) ANTI-SENSE: no (xi) SEQUENCE DESCRIPTION: SEQ ID NO: 14:

ATG GGT CTC ACC TCC GAA CTG CTT CCC CCT CTG TTC TTC CTG CTA         45
Met Gly Leu Thr Ser Gln Leu Leu Pro Pro Leu Phe Phe Leu Leu
  1                   5                  10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
 20                  25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
 35                  40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
 50                  55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
 65                  70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
 80                  85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
 95                 100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
```

```
125            130             135
TTC TTG GAA AGG CTA AAG ACG ATC ATG GCA GAG AAA GCA TCA AAG      450
Phe Leu Glu Arg Leu Lys Thr Ile Met Ala Glu Lys Ala Ser Lys
140                 145             150

TGT TCG AGC TAG                                                  462
Cys Ser Ser End
153

(2) INFORMATION FOR SEQ ID NO: 15:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: IL-4/Y124Q (iii) HYPOTHETICAL: no (iv) ANTI-SENSE: no (xi) SEQUENCE DESCRIPTION: SEQ ID NO: 15:

ATG GGT CTC ACC TCC CAA CTG CTT CCC CCT CTG TTC TTC CTG CTA      45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC      90
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG      135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC      180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG      225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG      270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA      315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG      360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC      405
Asn Ser Cys Pro Val Lys Glu Ala Asn Gln Ser Thr Leu Glu Asn
125                 130                 135

TTC TTG GAA AGG CTA AAG ACG ATC ATG AGA GAG AAA CAA TCA AAG      450
Phe Leu Glu Arg Leu Lys Thr Ile Met Arg Glu Lys Gln Ser Lys
140                 145                 150

TGT TCG AGC TAG                                                  462
Cys Ser Ser End
153

(2) INFORMATION FOR SEQ ID NO: 16:

(i) SEQUENCE CHARACTERISTICS:
        (A) LENGTH: 462
        (B) TYPE: nucleic acid
        (C) STRANDEDNESS: single
```

(D) TOPOLOGY: linear (ii) MOLECULE TYPE: cDNA
        (A) DESCRIPTION: IL-4/Y124R (iii) HYPOTHETICAL: no (iv) ANTI-SENSE: no (xi) SEQUENCE DESCRIPTION: SEQ ID NO: 16:

```
ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20              25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
35              40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50              55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65              70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80              85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95              100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110             115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125             130                 135

TTC TTG GAA AGG CTA AAG ACG ATC ATG AGA GAG AAA CGA TCA AAG        450
Phe Leu Glu Arg Leu Lys Thr Ile Met Arg Glu Lys Arg Ser Lys
140             145                 150

TGT TCG AGC TAG                                                    462
Cys Ser Ser End
153
```

(2) INFORMATION FOR SEQ ID NO: 17:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: IL-4/Y124S (iii) HYPOTHETICAL: no (iv) ANTI-SENSE: no (xi) SEQUENCE DESCRIPTION: SEQ ID NO: 17:

```
ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
```

```
                20                    25                    30

TTA CAG GAG ATC ATC AAA ACT TTG AAC AGC CTC ACA GAG CAG AAG         135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC         180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG         225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG         270
Leu Arg Gln Phe Tyr Ser His His Glu Lys Asp Thr Arg Cys Leu
80                  85                  90

GGT GCG ACT GCA CAG CAG TTC CAC AGG CAC AAG CAG CTG ATC CGA         315
Gly Ala Thr Ala Gln Gln Phe His Arg His Lys Gln Leu Ile Arg
95                  100                 105

TTC CTG AAA CGG CTC GAC AGG AAC CTC TGG GGC CTG GCG GGC TTG         360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC         405
Asn Ser Cys Pro Val Lys Glu Ala Asn Gln Ser Thr Leu Glu Asn
125                 130                 135

TTC TTG GAA AGG CTA AAG ACG ATC ATG AGA GAG AAA TCA TCA AAG         450
Phe Leu Glu Arg Leu Lys Thr Ile Met Arg Glu Lys Ser Ser Lys
140                 145                 150

TGT TCG AGC TAG                                                     462
Cys Ser Ser End
153

(2) INFORMATION FOR SEQ ID NO: 18:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: IL-4/Y124T (iii) HYPOTHETICAL: no (iv) ANTI-SENSE: no (xi) SEQUENCE DESCRIPTION: SEQ ID NO: 18:

ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
1                   5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20                  25                  30

TTA CAG GAG ATC ATC AAA ACT TTG AAC AGC CTC ACA GAG CAG AAG         135
Leu Gln Glu Ile Ile Lys Thr Leu Asn Ser Leu Thr Glu Gln Lys
35                  40                  45

ACT CTG TGC ACC GAG TTG ACC GTA ACA GAC ATC TTT GCT GCC TCC         180
Thr Leu Cys Thr Glu Leu Thr Val Thr Asp Ile Phe Ala Ala Ser
50                  55                  60

AAG AAC ACA ACT GAG AAG GAA ACC TTC TGC AGG GCT GCG ACT GTG         225
Lys Asn Thr Thr Glu Lys Glu Thr Phe Cys Arg Ala Ala Thr Val
65                  70                  75

CTC CGG CAG TTC TAC AGC CAC CAT GAG AAG GAC ACT CGC TGC CTG         270
Leu Arg Gln Phe Tyr Ser His His Glu Lys Asp Thr Arg Cys Leu
80                  85                  90
```

```
GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
 95                 100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125                 130                 135

TTC TTG GAA AGG CTA AAG ACG ATC ATG AGA GAG AAA ACA TCA AAG        450
Phe Leu Glu Arg Leu Lys Thr Ile Met Arg Glu Lys Thr Ser Lys
140                 145                 150

TGT TCG AGC TAG                                                    462
Cys Ser Ser End
153

(2) INFORMATION FOR SEQ ID NO: 19:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
        (A) DESCRIPTION: IL-4/Y124A/S125A (iii) HYPOTHETICAL: no (iv) ANTI-SENSE: no (xi) SEQUENCE DESCRIPTION: SEQ ID NO: 19:

ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
  1                 5                  10                 15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
 20                 25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
 35                 40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
 50                 55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
 65                 70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
 80                 85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
 95                 100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110                 115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125                 130                 135

TTC TTG GAA AGG CTA AAG ACG ATC ATG AGA GAG AAA GCT GCT AAG        450
Phe Leu Glu Arg Leu Lys Thr Ile Met Arg Glu Lys Ala Ala Lys
140                 145                 150
```

```
TGT TCG AGC TAG                                                    462
Cys Ser Ser End
153

(2) INFORMATION FOR SEQ ID NO: 20:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
         (A) DESCRIPTION: IL-4/T13D/R121E (iii) HYPOTHETICAL: no (iv) ANTI-SENSE: no (xi) SEQUENCE DESCRIPTION: SEQ ID NO: 20:

ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20              25                  30

TTA CAG GAG ATC ATC AAA GAT TTG AAC AGC CTC ACA GAG CAG AAG        135
Leu Gln Glu Ile Ile Lys Asp Leu Asn Ser Leu Thr Glu Gln Lys
35              40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50              55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65              70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80              85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95              100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110             115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125             130                 135

TTC TTG GAA AGG CTA AAG ACG ATC ATG GAA GAG AAA TAT TCA AAG        450
Phe Leu Glu Arg Leu Lys Thr Ile Met Glu Glu Lys Tyr Ser Lys
140             145                 150

TGT TCG AGC TAG                                                    462
Cys Ser Ser End
153

(2) INFORMATION FOR SEQ ID NO: 21:

(i) SEQUENCE CHARACTERISTICS:
        (A) LENGTH: 462
        (B) TYPE: nucleic acid
        (C) STRANDEDNESS: single
        (D) TOPOLOGY: linear (ii) MOLECULE TYPE: cDNA
         (A) DESCRIPTION: hIL-4/R121T/E122F/Y124Q (iii) HYPOTHETICAL: no
```

(iv) ANTI-SENSE: no (xi) SEQUENCE DESCRIPTION: SEQ ID NO: 21:

```
ATG GGT CTC ACC TCC CAA CTG CTT CCC CCT CTG TTC TTC CTG CTA         45
Met Gly Leu Thr Ser Gln Leu Leu Pro Pro Leu Phe Phe Leu Leu
1               5                   10                  15

GCA TGT GCC GGC AAC TTT GTC CAC GGA CAC AAG TGC GAT ATC ACC         90
Ala Cys Ala Gly Asn Phe Val His Gly His Lys Cys Asp Ile Thr
20              25                  30

TTA CAG GAG ATC ATC AAA ACT TTG AAC AGC CTC ACA GAG CAG AAG        135
Leu Gln Glu Ile Ile Lys Thr Leu Asn Ser Leu Thr Glu Gln Lys
35              40                  45

ACT CTG TGC ACC GAG TTG ACC GTA ACA GAC ATC TTT GCT GCC TCC        180
Thr Leu Cys Thr Glu Leu Thr Val Thr Asp Ile Phe Ala Ala Ser
50              55                  60

AAG AAC ACA ACT GAG AAG GAA ACC TTC TGC AGG GCT GCG ACT GTG        225
Lys Asn Thr Thr Glu Lys Glu Thr Phe Cys Arg Ala Ala Thr Val
65              70                  75

CTC CGG CAG TTC TAC AGC CAC CAT GAG AAG GAC ACT CGC TGC CTG        270
Leu Arg Gln Phe Tyr Ser His His Glu Lys Asp Thr Arg Cys Leu
80              85                  90

GGT GCG ACT GCA CAG CAG TTC CAC AGG CAC AAG CAG CTG ATC CGA        315
Gly Ala Thr Ala Gln Gln Phe His Arg His Lys Gln Leu Ile Arg
95              100                 105

TTC CTG AAA CGG CTC GAC AGG AAC CTC TGG GGC CTG GCG GGC TTG        360
Phe Leu Lys Arg Leu Asp Arg Asn Leu Trp Gly Leu Ala Gly Leu
110             115                 120

AAT TCC TGT CCT GTG AAG GAA GCC AAC CAG AGT ACG TTG GAA AAC        405
Asn Ser Cys Pro Val Lys Glu Ala Asn Gln Ser Thr Leu Glu Asn
125             130                 135

TTC TTG GAA AGG CTA AAG ACG ATC ATG ACC TTC AAA CAG TCA AAG        450
Phe Leu Glu Arg Leu Lys Thr Ile Met Thr Phe Lys Gln Ser Lys
140             145                 150

TGT TCG AGC TAG                                                    462
Cys Ser Ser End
153
```

(2) INFORMATION FOR SEQ ID NO: 22:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: cDNA
        (A) DESCRIPTION: 5' PCR Primer, IL-4

(iii) HYPOTHETICAL: no (iv) ANTI-SENSE: no (xi) SEQUENCE DESCRIPTION: SEQ ID NO: 22:

CGCGGATCCA TGGGTCTCAC CTCC                              24

(2) INFORMATION FOR SEQ ID NO: 23:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: cDNA (A) DESCRIPTION: 3' PCR Primer, IL-4

(iii) HYPOTHETICAL: no (iv) ANTI-SENSE: no (xi) SEQUENCE DESCRIPTION: SEQ ID NO: 23:

CGCTCTAGAC TAGCTCGAAC ACTTTGAAT                                               29

(2) INFORMATION FOR SEQ ID NO: 24:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121A (iii) HYPOTHETICAL: no (iv) ANTI-SENSE: no (xi) SEQUENCE DESCRIPTION: SEQ ID NO: 24:

CTAAAGACGA TCATGGCTGA GAAATATT                                                28

(2) INFORMATION FOR SEQ ID NO: 25:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121D (iii) HYPOTHETICAL: no (iv) ANTI-SENSE: no (xi) SEQUENCE DESCRIPTION: SEQ ID NO: 25:

GCTAAAGACG ATCATGGACG AGAAATATTC                                              30

(2) INFORMATION FOR SEQ ID NO: 26:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121E (iii) HYPOTHETICAL: no (iv) ANTI-SENSE: no (xi) SEQUENCE DESCRIPTION: SEQ ID NO: 26:

GCTAAAGACG ATCATGGAAG AGAAATATTC                                              30

(2) INFORMATION FOR SEQ ID NO: 27:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
            (A) DESCRIPTION: Mutagenesis Primer, IL-4/R121F (iii) HYPOTHETICAL: no (iv) ANTI-SENSE: no (xi) SEQUENCE DESCRIPTION: SEQ ID NO: 27:

CTAAAGACGA TCATGTTTGA GAAATATT                                              28

(2) INFORMATION FOR SEQ ID NO: 28:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121H (iii) HYPOTHETICAL: no (iv) ANTI-SENSE: no (xi) SEQUENCE DESCRIPTION: SEQ ID NO: 28:

CTAAAGACGA TCATGCACGA GAAATATT                                              28

(2) INFORMATION FOR SEQ ID NO: 29:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121I (iii) HYPOTHETICAL: no (iv) ANTI-SENSE: no (xi) SEQUENCE DESCRIPTION: SEQ ID NO: 29:

CTAAAGACGA TCATGATAGA GAAATATT                                              28

(2) INFORMATION FOR SEQ ID NO: 30:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121K (iii) HYPOTHETICAL: no (iv) ANTI-SENSE: no (xi) SEQUENCE DESCRIPTION: SEQ ID NO: 30:

CTAAAGACGA TCATGAAAGA GAAATATT                                              28

(2) INFORMATION FOR SEQ ID NO: 31:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
              (A) DESCRIPTION: Mutagenesis Primer, IL-4/R121N (iii) HYPOTHETICAL: no (iv) ANTI-SENSE: no (xi) SEQUENCE DESCRIPTION: SEQ ID NO: 31:

CTAAAGACGA TCATGAACGA GAAATATT                                              28

(2) INFORMATION FOR SEQ ID NO: 32:

(i) SEQUENCE CHARACTERISTICS:
              (A) LENGTH: 30
              (B) TYPE: nucleic acid
              (C) STRANDEDNESS: single
              (D) TOPOLOGY: linear (ii) MOLECULE TYPE: cDNA
              (A) DESCRIPTION: Mutagenesis Primer, IL-4/R121P (iii) HYPOTHETICAL: no (iv) ANTI-SENSE: no (xi) SEQUENCE DESCRIPTION: SEQ ID NO: 32:

GCTAAAGACG ATCATGCCAG AGAAATATTC                                            30

(2) INFORMATION FOR SEQ ID NO: 33:

(i) SEQUENCE CHARACTERISTICS:
              (A) LENGTH: 28
              (B) TYPE: nucleic acid
              (C) STRANDEDNESS: single
              (D) TOPOLOGY: linear (ii) MOLECULE TYPE: cDNA
              (A) DESCRIPTION: Mutagenesis Primer, IL-4/R121T (iii) HYPOTHETICAL: no (iv) ANTI-SENSE: no (xi) SEQUENCE DESCRIPTION: SEQ ID NO: 33:

CTAAAGACGA TCATGACTGA GAAATATT                                              28

(2) INFORMATION FOR SEQ ID NO: 34:

(i) SEQUENCE CHARACTERISTICS:
              (A) LENGTH: 28
              (B) TYPE: nucleic acid
              (C) STRANDEDNESS: single
              (D) TOPOLOGY: linear (ii) MOLECULE TYPE: cDNA
              (A) DESCRIPTION: Mutagenesis Primer, IL-4/R121W (iii) HYPOTHETICAL: no (iv) ANTI-SENSE: no (xi) SEQUENCE DESCRIPTION: SEQ ID NO: 34:

CTAAAGACGA TCATGTGGGA GAAATATT                                              28

(2) INFORMATION FOR SEQ ID NO: 35:

(i) SEQUENCE CHARACTERISTICS:
              (A) LENGTH: 28
              (B) TYPE: nucleic acid
              (C) STRANDEDNESS: single (D) TOPOLOGY: linear (ii) MOLECULE TYPE: cDNA
          (A) DESCRIPTION: Mutagenesis Primer, IL-4/Y124A (iii) HYPOTHETICAL: no (iv) ANTI-SENSE: no (xi) SEQUENCE DESCRIPTION: SEQ ID NO: 35:

ATCATGAGAG AGAAAGCATC AAAGTGTT                                           28

(2) INFORMATION FOR SEQ ID NO: 36:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: cDNA
          (A) DESCRIPTION: Mutagenesis Primer, IL-4/Y124Q (iii) HYPOTHETICAL: no (iv) ANTI-SENSE: no (xi) SEQUENCE DESCRIPTION: SEQ ID NO: 36:

ATCATGAGAG AGAAACAATC AAAGTGTT                                           28

(2) INFORMATION FOR SEQ ID NO: 37:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: cDNA
          (A) DESCRIPTION: Mutagenesis Primer, IL-4/Y124R (iii) HYPOTHETICAL: no (iv) ANTI-SENSE: no (xi) SEQUENCE DESCRIPTION: SEQ ID NO: 37:

ATCATGAGAG AGAAACGATC AAAGTGTT                                           28

(2) INFORMATION FOR SEQ ID NO: 38:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: cDNA
          (A) DESCRIPTION: Mutagenesis Primer, IL-4/Y124S (iii) HYPOTHETICAL: no (iv) ANTI-SENSE: no (xi) SEQUENCE DESCRIPTION: SEQ ID NO: 38:

ATCATGAGAG AGAAATCATC AAAGTGTT                                           28

(2) INFORMATION FOR SEQ ID NO: 39:

(i) SEQUENCE CHARACTERISTICS:
          (A) LENGTH: 28
          (B) TYPE: nucleic acid (C) STRANDEDNESS: single
    (D) TOPOLOGY: linear (ii) MOLECULE TYPE: cDNA
    (A) DESCRIPTION: Mutagenesis Primer, IL-4/Y124T (iii) HYPOTHETICAL: no (iv) ANTI-SENSE: no (xi) SEQUENCE DESCRIPTION: SEQ ID NO: 39:

ATCATGAGAG AGAAAACATC AAAGTGTT                                      28

(2) INFORMATION FOR SEQ ID NO: 40:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/Y124A/S125A (iii) HYPOTHETICAL: no (iv) ANTI-SENSE: no (xi) SEQUENCE DESCRIPTION: SEQ ID NO: 40:

CGATCATGAG AGAGAAAGCT GCTAAGTGTT CGA                                33

(2) INFORMATION FOR SEQ ID NO: 41:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/T13D: T13D
            substitution (iii) HYPOTHETICAL: no (iv) ANTI-SENSE: no (xi) SEQUENCE DESCRIPTION: SEQ ID NO: 41:

CAGGAGATCA TCAAAGATTT GAACAGCC                                      28

(2) INFORMATION FOR SEQ ID NO: 42:

(i) SEQUENCE CHARACTERISTICS:
        (A) LENGTH: 34
        (B) TYPE: nucleic acid
        (C) STRANDEDNESS: single
        (D) TOPOLOGY: linear (ii) MOLECULE TYPE: cDNA
        (A) DESCRIPTION: Mutagenesis Primer, IL-4/R121T/E122F/Y124Q (iii) HYPOTHETICAL: no (iv) ANTI-SENSE: no (xi) SEQUENCE DESCRIPTION: SEQ ID NO: 42:

GCTAAAGACG ATCATGACCT TCAAACAGTC AAAG                               34